United States Patent [19]

Yamada et al.

[11] Patent Number: 5,097,836
[45] Date of Patent: Mar. 24, 1992

[54] UNTRASOUND DIAGNOSTIC EQUIPMENT FOR CALCULATING AND DISPLAYING INTEGRATED BACKSCATTER OR SCATTERING COEFFICIENTS BY USING SCATTERING POWER OR SCATTERING POWER SPECTRUM OF BLOOD

[75] Inventors: Isamu Yamada; Akira Shiba; Keiichi Murakami, all of Kawasaki; Takaki Shimura, Tokyo, all of Japan

[73] Assignee: Fujitsu Limited, Kawasaki, Japan

[21] Appl. No.: 480,455

[22] Filed: Feb. 15, 1990

[30] Foreign Application Priority Data

Feb. 16, 1989 [JP] Japan .................................. 1-36694
Feb. 16, 1989 [JP] Japan .................................. 1-36695

[51] Int. Cl.[5] ................................................. A61B 8/00
[52] U.S. Cl. ........................... 128/660.07; 128/661.04
[58] Field of Search ....................... 128/660.01, 660.04, 128/660.06, 660.07, 661.09; 73/597, 599, 602, 620

[56] References Cited

U.S. PATENT DOCUMENTS

| | | | |
|---|---|---|---|
| 4,470,303 | 9/1984 | O'Donnell | 73/602 |
| 4,803,994 | 2/1989 | Burke | 128/660.06 |
| 4,862,892 | 9/1989 | Green | 128/660.06 |
| 4,867,167 | 9/1989 | Magnin | 128/660.26 |
| 4,873,984 | 10/1989 | Hunt et al. | 128/660.07 |
| 4,881,549 | 11/1989 | Rhyne | 128/660.07 |

FOREIGN PATENT DOCUMENTS

| | | |
|---|---|---|
| 0099764 | 1/1984 | European Pat. Off. . |
| 0248623 | 12/1987 | European Pat. Off. . |
| 0349321 | 1/1990 | European Pat. Off. . |

OTHER PUBLICATIONS

"A Real-Time Integrated Backscatter Measurement System for Quantitative Cardiac Tissue Characterization", Thomas III et al., IEEE Transactions on Ultrasonics, Ferroeletrics and Frequency Control, vol. UFF-C-33, No. 1, Jan., 1986, pp. 27-32.

"The Myocardial Signature: Absolute Backscatter, Cyclical Variation, Frequency Variation, and Statistics", Ultrasonic Imaging 8, vol. 8, No. 2, Apr., 1986, pp. 107-120.

"Effects of Coronary Artery Occlusion and Reperfusion on Cardiac Cycle-Dependent Variation of Myocardial Ultrasonic Backscatter", Glueck et al., Circulation Research, vol. 56, No. 5, May, 1985, pp. 683-689.

"Regional Differences in the Cyclic Variation of Myocardial Backscatter That Parallel Regional Differences in Contractile Performance", Mottley et al., J. Acoust. Soc. Am. 76 (6), Dec., 1984, pp. 1617-1623.

"Sensitive Detection of the Effects of Reperfusion on Myocardium by Ultrasonic Tissue Characterization with Integrated Backscatter", Wickline et al., Circulation, vol. 74, No. 2, Aug, 1986, pp. 389-400.

Primary Examiner—Francis Jaworski
Attorney, Agent, or Firm—Armstrong, Nikaido, Marmelstein, Kubovcik & Murray

[57] ABSTRACT

Ultrasound diagnostic equipment comprises a tissue power unit for calculating tissue scattering power of tissues of an object of measurement in an organ, a blood power unit for calculating scattering power of blood in the organ and estimating blood scattering power at a portion of the tissues of the object of measurement by using the calculated scattering power of the blood, an integrated backscatter unit for normalizing the tissue scattering power by using the estimated blood scattering power and calculating an integrated backscatter by the normalized tissue scattering power, and a display unit for displaying the integrated backscatter. Therefore, the integrated backscatter of the tissues can be quantitatively estimated without being influenced by attenuation. Furthermore, this estimated quantitative integrated backscatter of the tissues is displayed on the display unit accompanied with a B-mode image, an electrocardiogram, and the like, so that diagnostic accuracy can be increased.

52 Claims, 29 Drawing Sheets

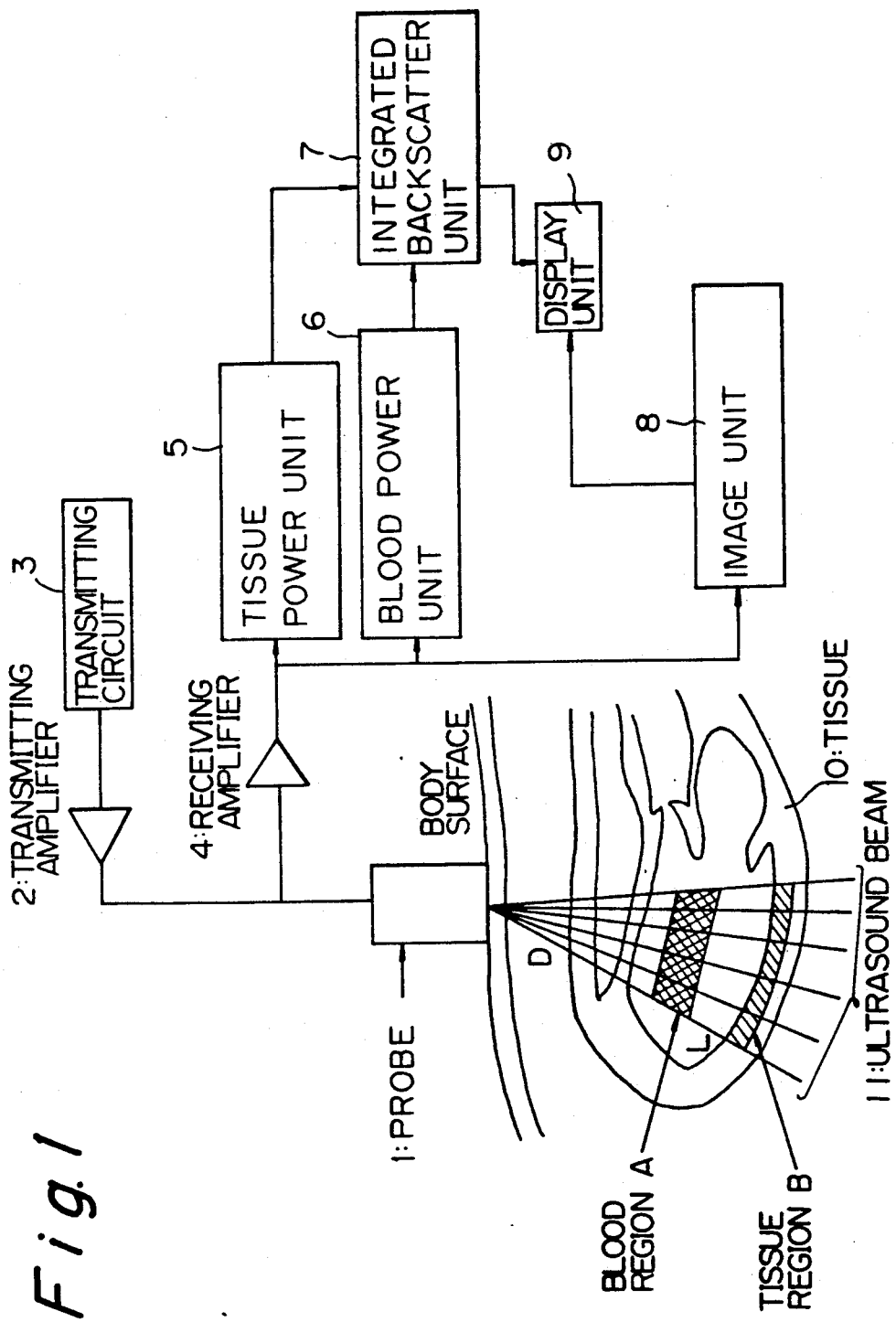

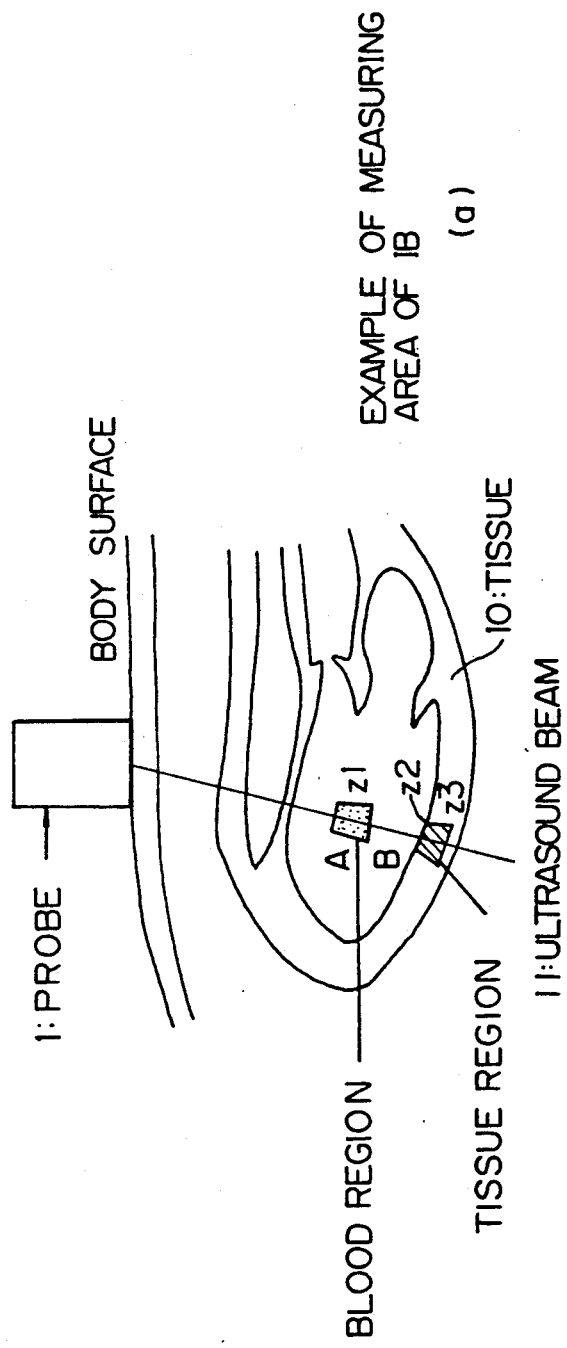

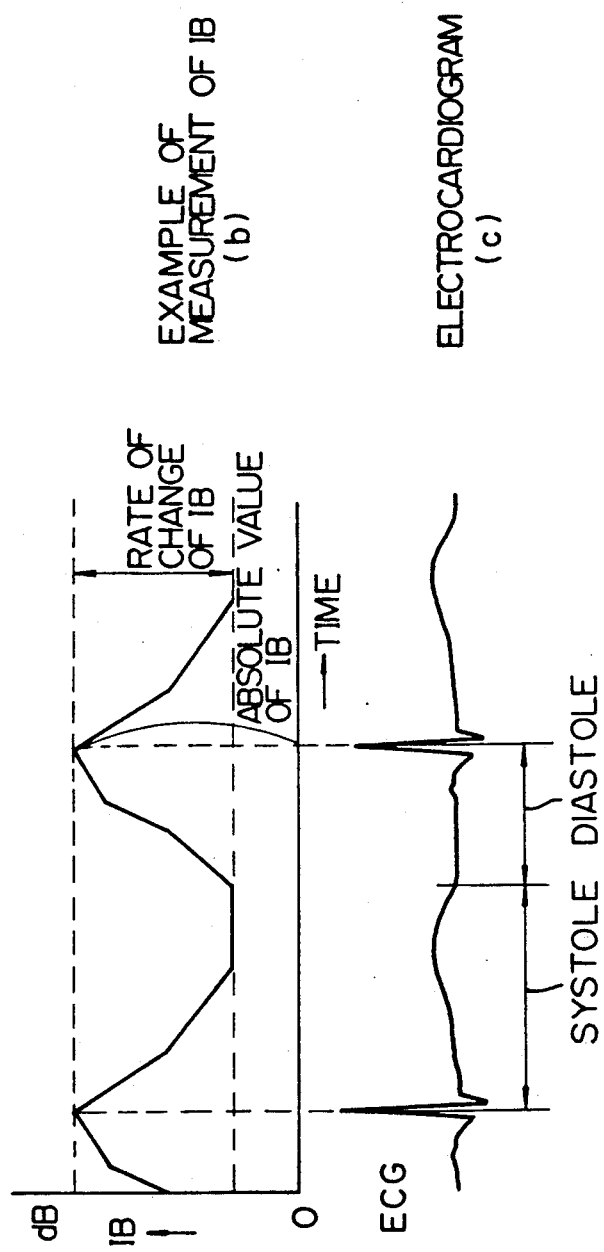

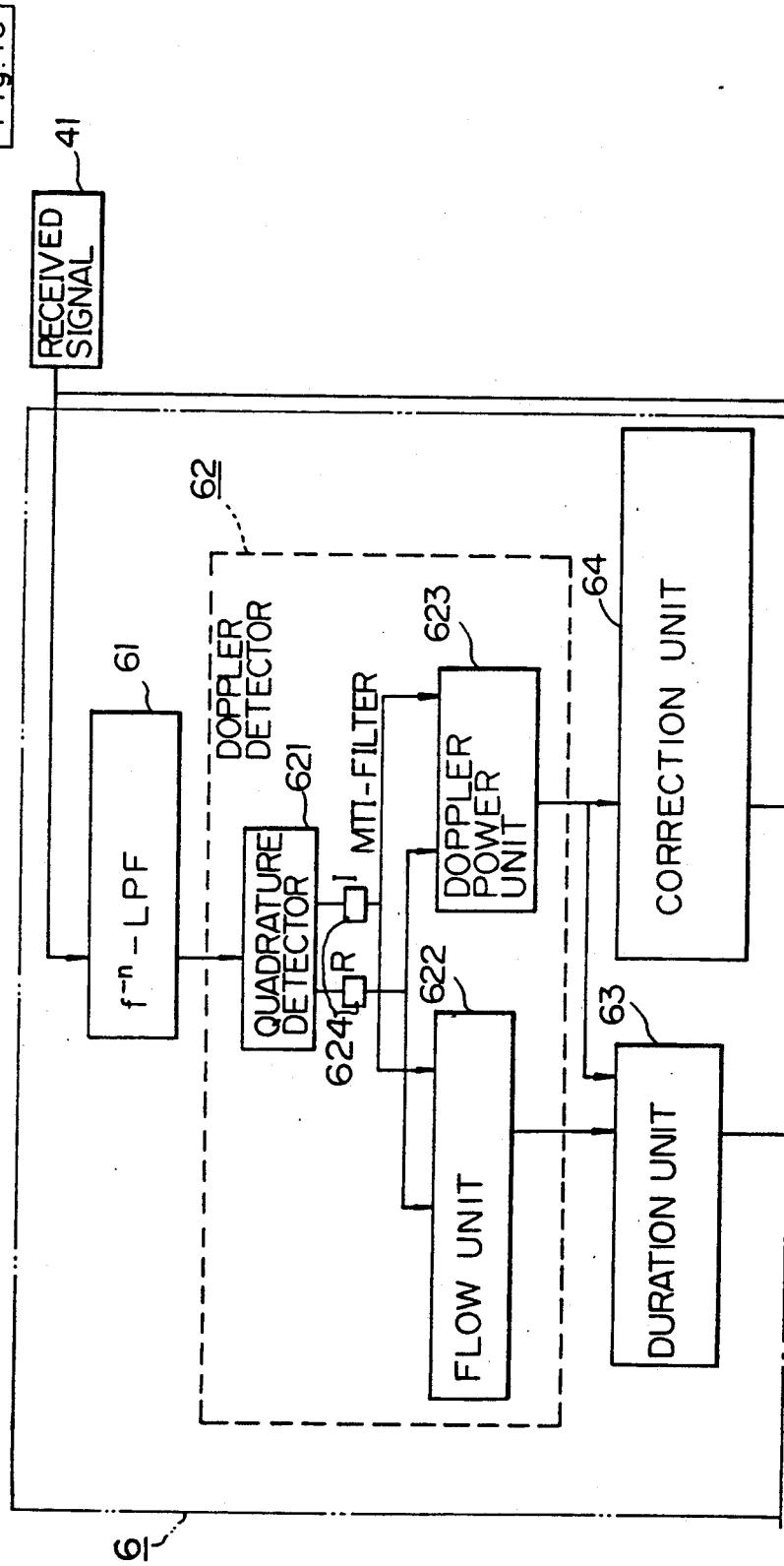

(a)

(b)
ELECTROCARDIOGRAM

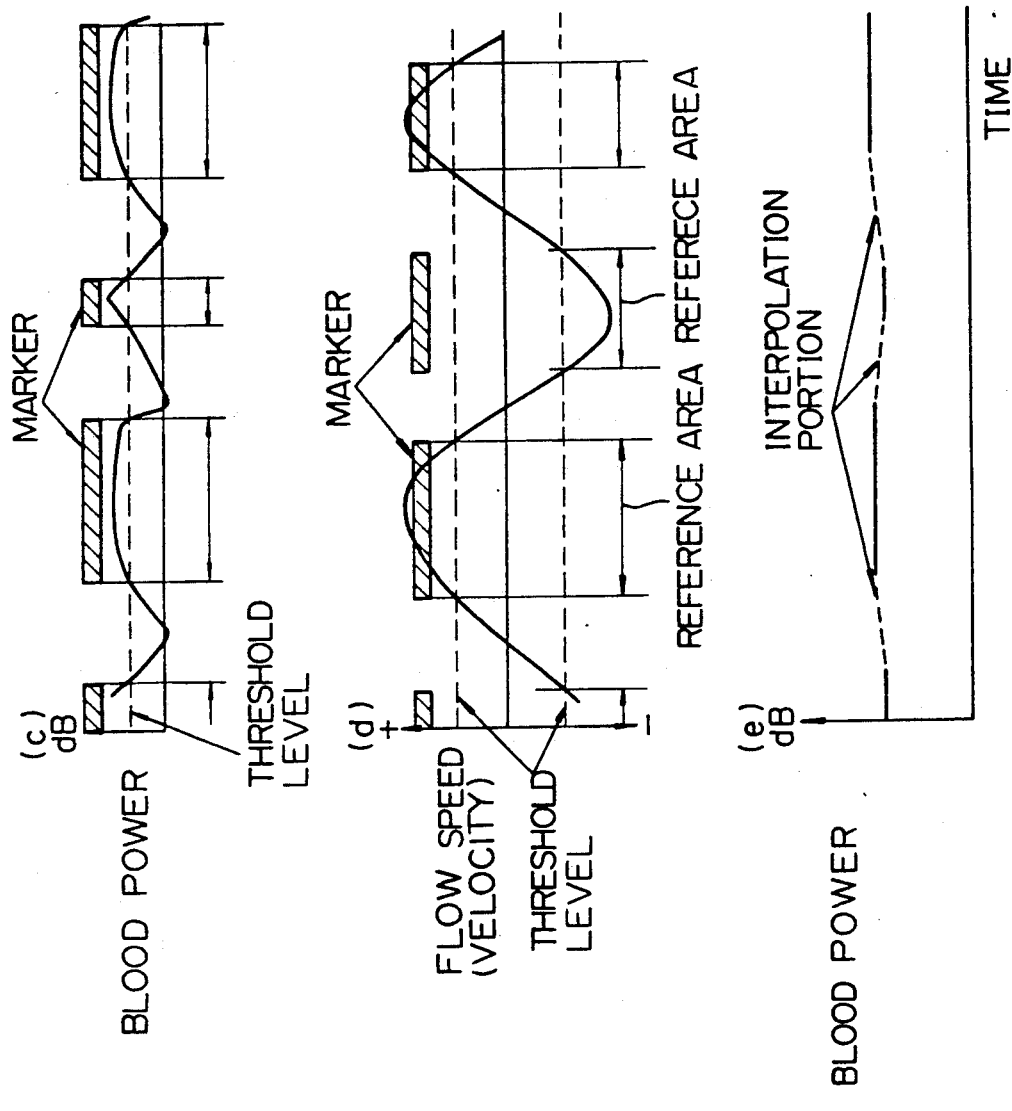

(a)

(b)
ELECTROCARDIOGRAM

Fig.6C
(c) IB OF BLOOD REFERENCE IN T₁ / IB OF BLOOD REFERENCE IN T₂
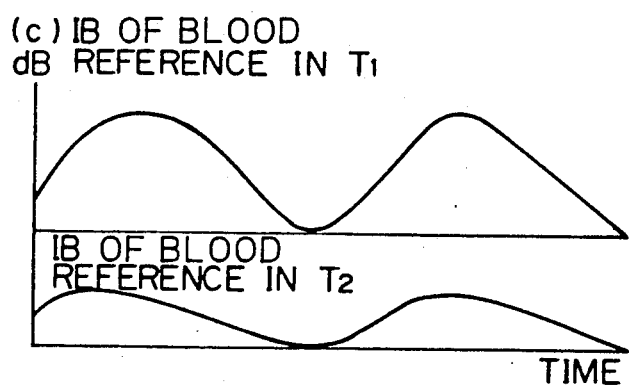
Fig.6D
(d) MARKER IN BLOOD REFERENCE
Fig.6E
(e) COLOR CODED IMAGE OF IB ON M-MODE IMAGE
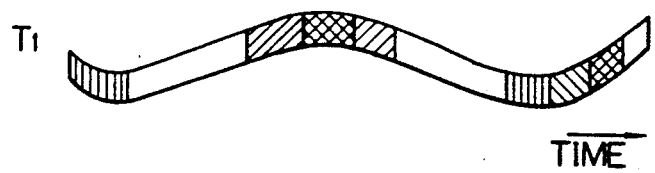

(a) EXAMPLE OF DISPLAY ON B-MODE IMAGE (b) DESIGNATION METHOD OF CARDIAC MUSCLE DIRECTION MARKER

AN EXAMPLE OF
RELATION BETWEEN ANGLE
AND INTEGRATED BACKSCATTER
CORRECTION FACTOR (c)

AN EXAMPLE OF
SCATTERING PARAMETER
PROFILE IN THE DIRECTION OF CARDIAC
MUSCLE DIRECTION
MARKER (d)

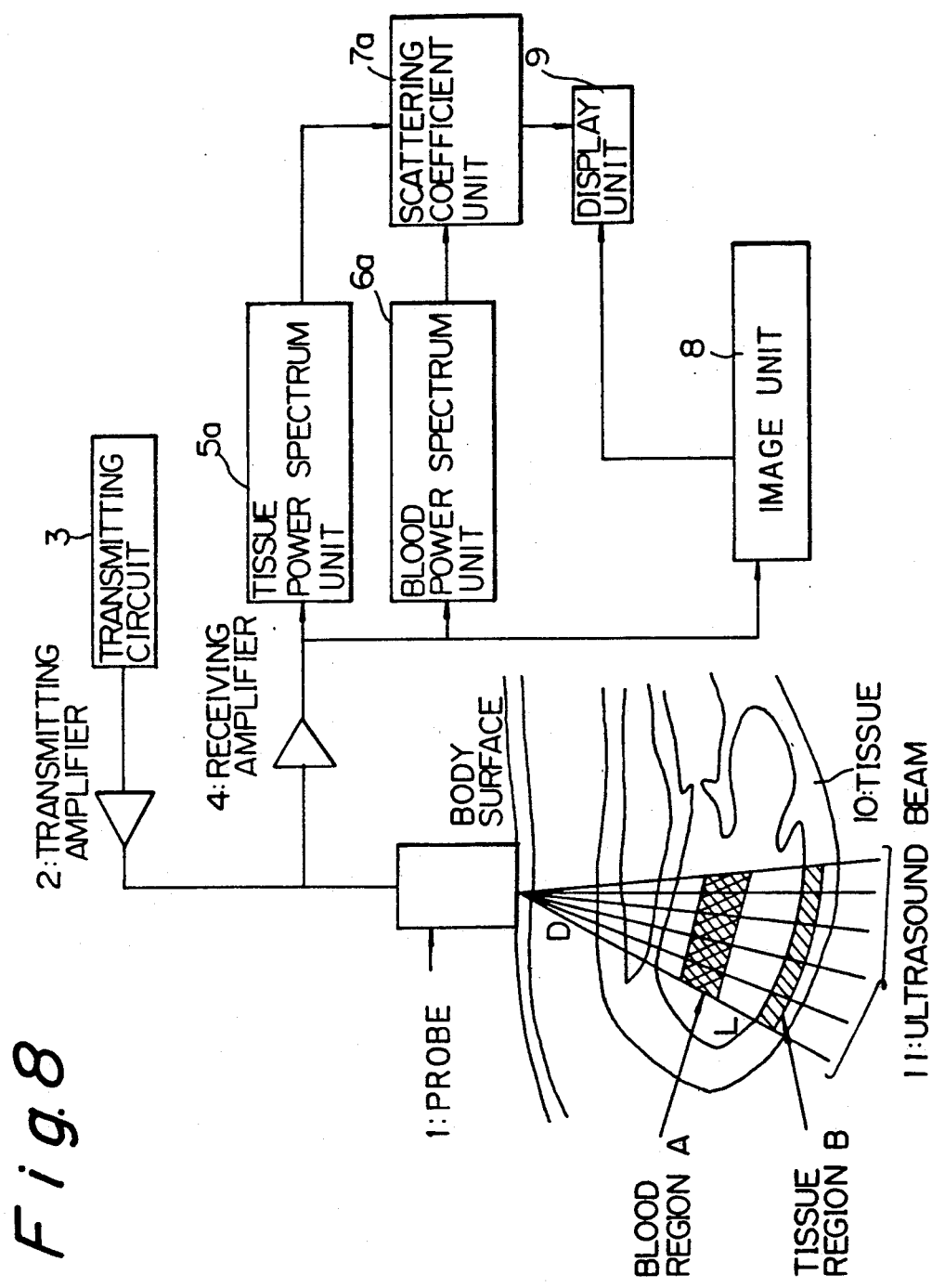

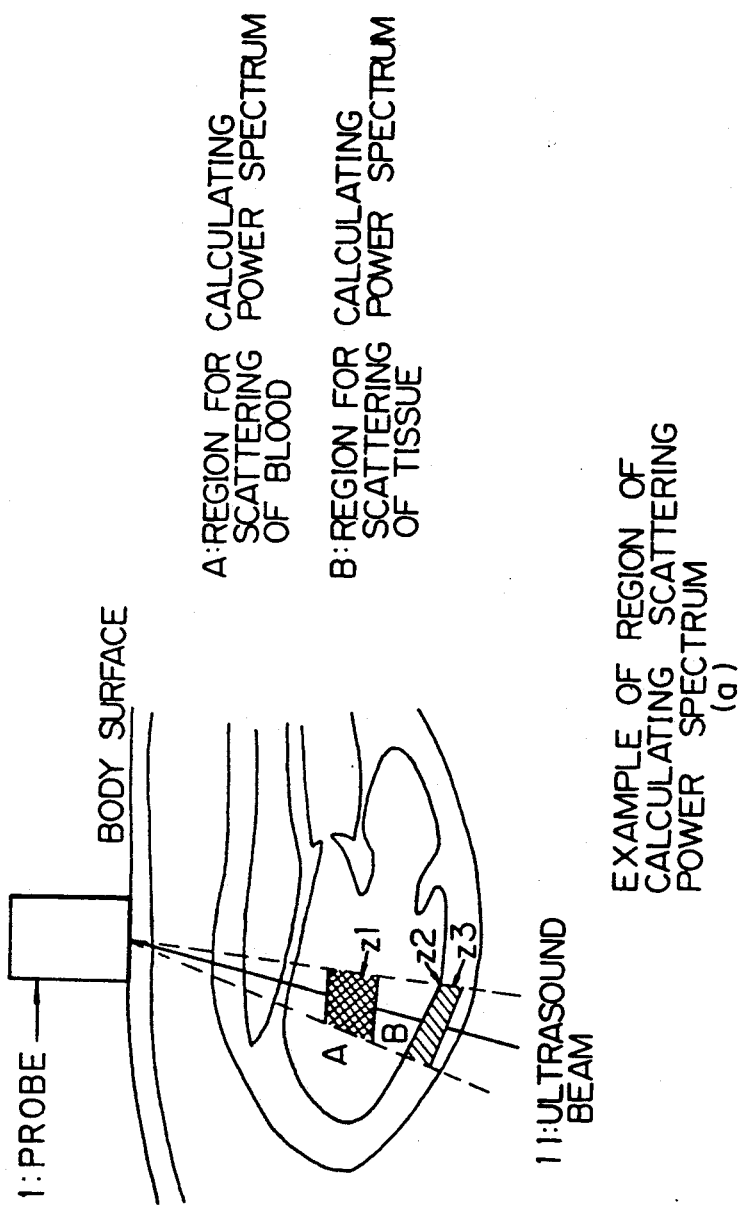

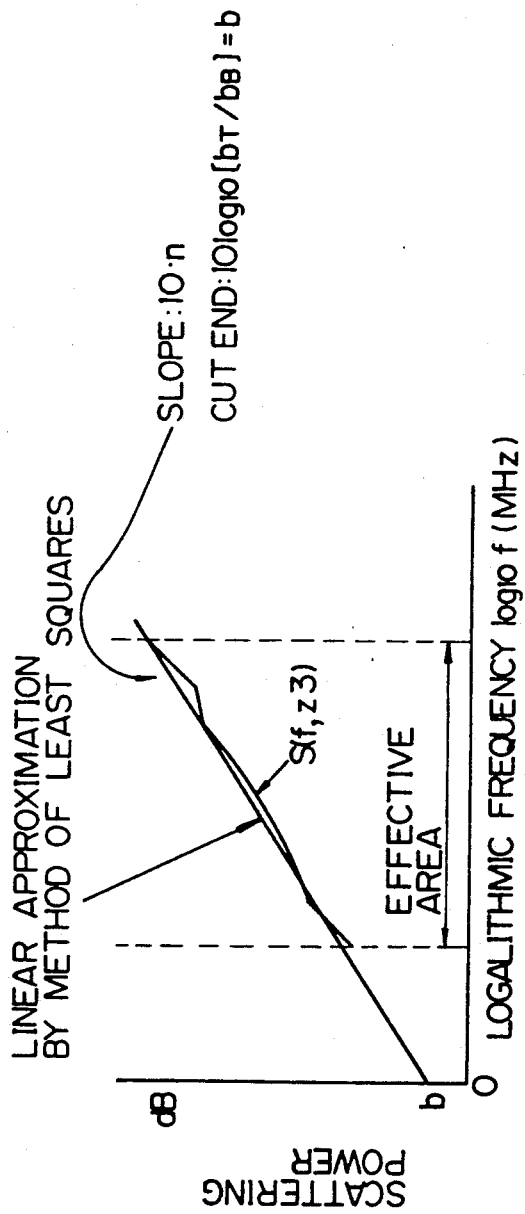

(a)

(b)

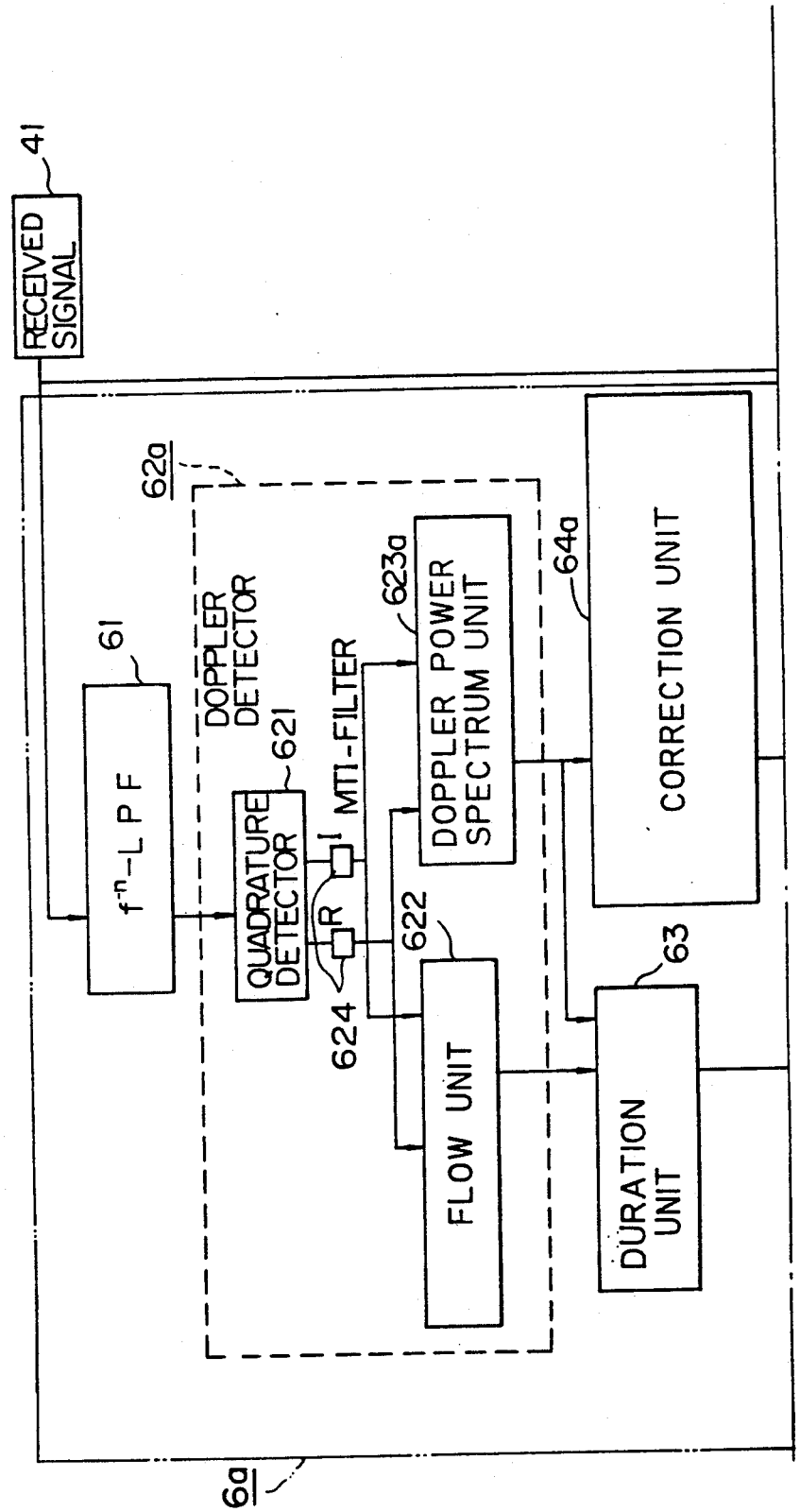

(a) REAL COMPONENT AND IMAGINAL COMPONENT OF QUADRATURE DETECTION (b) SCATTERING POWER SPECTRUM OF BLOOD (c) SCATTERING POWER SPECTRUM OF TISSUE (d) FREQUENCY SHIFTED BLOOD POWER SPECTRUM (e) AVERAGED TISSUE SCATTERING POWER SPECTRUM ON FREQUENCY AXIS (a)

(b)
ELECTROCARDIOGRAM

SYSTOLE  DIASTOLE (a)

(b)
ELECTROCARDIOGRAM

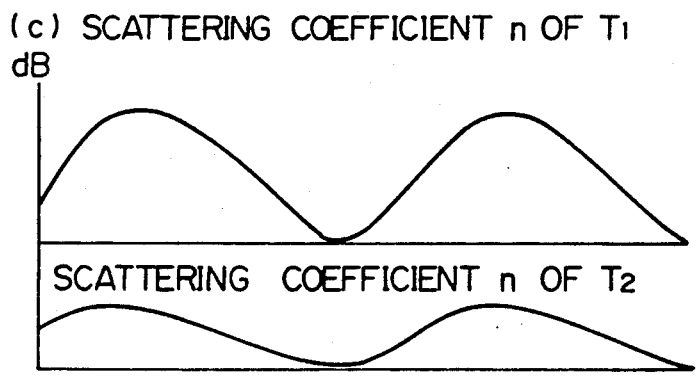
Fig.14C
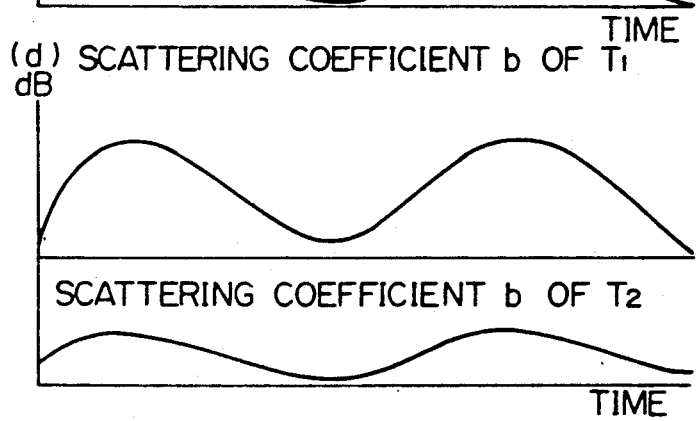
Fig.14D
Fig.14E
Fig.14F
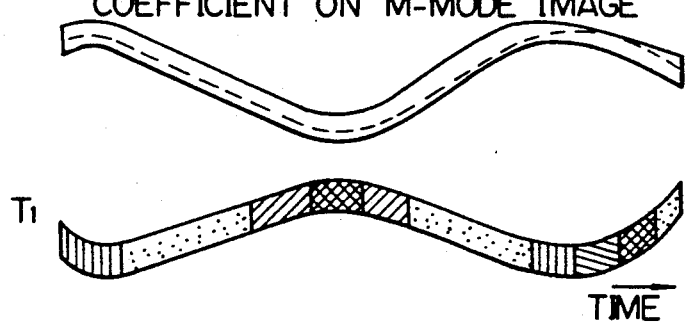

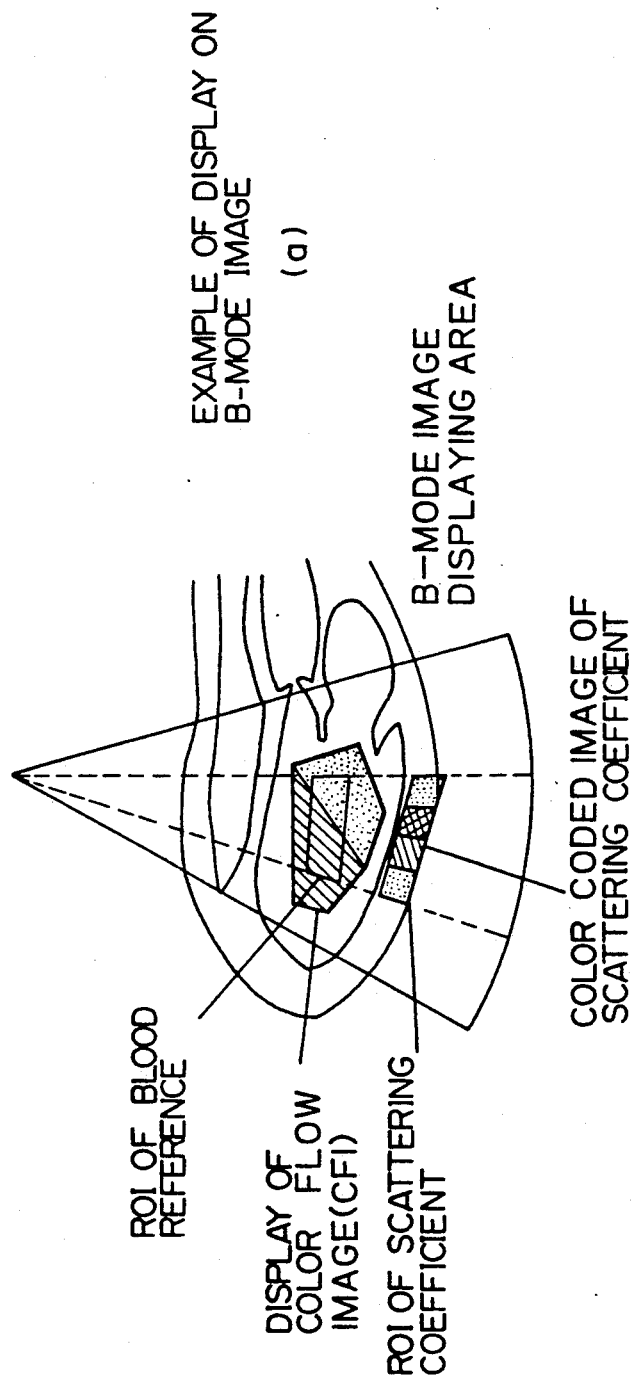

DESIGNATION METHOD OF
CARDIAC MUSCLE DIRECTION
MARKER (b)

AN EXAMPLE OF
RELATION BETWEEN
ANGLE AND SCATTERING
STRENGTH CORRECTION
FACTOR (c)

AN EXAMPLE OF SCATTERING
COEFFICIENT PROFILE IN THE
DIRECTION OF CARDIAC
MUSCLE DIRECTION MARKER (d)

UNTRASOUND DIAGNOSTIC EQUIPMENT FOR CALCULATING AND DISPLAYING INTEGRATED BACKSCATTER OR SCATTERING COEFFICIENTS BY USING SCATTERING POWER OR SCATTERING POWER SPECTRUM OF BLOOD

BACKGROUND OF THE INVENTION

1. Field of the Invention

The present invention relates to ultrasound diagnostic equipment, more particularly, to ultrasound diagnostic equipment for displaying an integrated backscatter (IB) or scattering coefficient b and n of tissues of an object to be measured in an organ by using scattering power or scattering power spectrum of blood.

In diagnostic techniques using ultrasound waves, it is necessary to improve diagnostic accuracy by quantitative diagnosis of tissues.

Now, acoustic characteristics of tissues, especially, attenuation characteristics and scattering characteristics, are used to indicate the characteristics of the tissues. Note, the present invention relates to an apparatus for calculating an integrated backscatter IB, which is an acoustic characteristic, quantitatively and exactly and for displaying it. Further, the present invention relates to an apparatus for calculating coefficients b and n quantitatively and exactly and for displaying them, when defining scattering frequency characteristics of the acoustic characteristics to the following equation.

$$S(f) = b f^n$$

2. Description of the Related Art

Conventionally, when diagnosing a heart by using ultrasound waves and detecting scattering power of a cardiac wall by synchronizing with a heartbeat, it is known that a change in ultrasound scattering power (IB) of a cardiac wall portion of a myocardial infarction is different from that of a normal cardiac wall portion. Furthermore, conventionally when diagnosing a heart by using ultrasound waves and calculating scattering coefficients, it is known that the scattering coefficients b and n of a cardiac wall portion of a myocardial infarction are different from those of a normal cardiac wall portion.

However, when practically diagnosing the heart from a body surface by using ultrasound waves, the ultrasound waves are attenuated during passage from the body surface to a measurement portion. In addition, the degree of attenuation that occurs from the body surface to each measurement portion is different from the others, and thus an absolute value of the obtained result cannot exactly indicate a characteristic of the portion. In order to solve the above problem, a means to measure the scattering power, which has high accuracy and does not depend on the attenuation (attenuation characteristics), is required. Furthermore, in order to solve the above problem, a means to measure the scattering coefficients, which has high accuracy and does not depend on the attenuation, are also required.

SUMMARY OF THE INVENTION

It is an object of the present invention to provide ultrasound diagnostic equipment for calculating an integrated backscatter IB of tissues of an object of measurement in an organ exactly by normalizing scattering power of the tissues of the object of measurement by using the scattering power of blood which has definite ultrasound scattering characteristics, and for displaying it.

It is another object of the present invention to provide ultrasound diagnostic equipment for calculating scattering coefficients b and n of tissues of an object of measurement in an organ exactly by normalizing scattering power spectrum of the tissues of the object of measurement by using scattering power spectrum of blood which has definite ultrasound scattering characteristics, and for displaying them.

According to a first aspect of the present invention, there is provided ultrasound diagnostic equipment for calculating and displaying an integrated backscatter IB of an organ from received signals, which comprises a tissue power unit, supplied with the received signals, for calculating tissue scattering power of tissues of an object of measurement in the organ, a blood power unit, supplied with the received signals, for calculating scattering power of blood in the organ and estimating scattering power at a portion of the tissues of the object of measurement by using the calculated scattering power of the blood, an integrated backscatter unit, connected to the tissue power unit and the blood power unit, for normalizing the tissue scattering power by using the estimated blood scattering power, and for calculating an integrated backscatter IB by the normalized tissue scattering power. and a display unit, connected to the integrated backscatter unit, for displaying the integrated backscatter IB.

The tissue power unit may comprise a power unit, supplied with the received signal, for calculating scattering power of the tissues in the organ, and a tissue spatial average unit, connected to the power unit, for deriving a spatial average of the scattering powers of the tissues in the organ obtained by each scanning line.

The blood power unit may calculate an average of the blood scattering powers for each duration of blood flow speed exceeding threshold levels or for each duration of blood scattering power exceeding a threshold level, and estimating blood scattering power at the portion of the tissues of the object of measurement by using the calculated average scattering power of the blood.

The blood power unit may comprise a low pass filter having $f^{-n}$ characteristics, supplied with the received signals, a doppler detector, connected to the low pass filter, for calculating a blood flow speed and a blood flow power, a duration unit, connected to the doppler detector, for detecting a duration of blood flow speed exceeding threshold levels or a duration of blood flow power exceeding a threshold level, a correction unit, connected to the doppler detector, for correcting a variable factor of the blood scattering power by an individual difference of volume percentage of blood corpuscle in each human, or for correcting the scattering power of the blood against the blood flow speed, an external designation unit, for externally designating a duration where the blood scattering power is calculated, an average unit, connected to the duration unit, the correcting unit and the external designation unit, for averaging the scattering powers of the blood in a duration detected by the duration unit or designated by the external designation unit, an interpolation unit, connected to the average unit, for interpolating each average scattering power of the blood by an m-th order interpolation, an attenuation correction unit, connected to the interpolation unit, for correcting blood power in accordance with attenuation from the position of the blood of the position of the tissues, and a blood spatial average unit, connected to the attenuation correction unit and the integrated backscatter unit, for deriving a spatial average of the scattering powers of the blood obtained by each scanning line. The doppler detector may include a quadrature detector, an MTI-filter, a flow unit, and a doppler power unit.

The integrated backscatter unit may comprise an ROI-setting unit, supplied with the received signals, for designating an ROI (region of interest) of a marker, and for activating a function of moving the ROI or the marker in accordance with a wall-movement, a normalizing unit, connected to the tissue power unit and the blood power unit, for calculating an integrated backscatter IB, and an angle correction unit, connected to the normalizing unit, for correcting the integrated backscatter IB according to an angle between a cardiac muscle direction and an ultrasound beam.

The ultrasound diagnostic equipment may further comprise an image unit, supplied with the received signals, for generating a B-mode image, a color flow image and/or an M-mode image, so that the display unit can display both the integrated backscatter IB of the tissues and the B-mode image, the color flow image and/or the M-mode image.

The display unit can display the integrated backscatter IB of the tissues as a time varying graph. The display unit may display the integrated backscatter IB of the tissues accompanied with an electrocardiogram.

The display unit may display a marker or a color at a duration of a blood flow speed's exceeding threshold levels or a duration of a blood flow power's exceeding a threshold level. The display unit may display an one-dimensional integrated backscatter IB profile along a designated direction. The ultrasound diagnostic equipment may be used for diagnosing a myocardial infarction of a heart.

According to the first aspect of the present invention, there is also provided ultrasound diagnostic equipment for calculating and displaying an integrated backscatter IB of an organ from received signals, which comprise a probe contacted to a body surface over the organ for radiation an ultrasound beam to an optional portion using electrical pulses and receiving ultrasound waves scattered from the optional portion and converting the received ultrasound waves to received electrical signals, a transmitting circuit, for generating electrical pulses in accordance with a predetermined timing, a transmitting amplifier connected between the probe and the transmitting circuit for amplifying the electrical pulses and driving the probe, a receiving amplifier connected to the probe for amplifying electrical signals received by the probe, a tissue power unit connected to the receiving amplifier for calculating scattering power of a tissue region of an object of measurement in the organ, a blood power unit connected to the receiving amplifier for calculating scattering power of a blood region of the object of measurement in the organ and for estimating blood scattering power at the tissue region by using the calculated scattering power of the blood, an integrated backscatter unit connected to the tissue power unit and the blood power unit for normalizing the tissue scattering power calculated by the tissue power unit by using the blood scattering power estimated by the blood power unit, and for calculating an integrated backscatter IB an image unit, connected to the receiving amplifier for generating a B-mode image, a color flow image and/or an M-mode image, and a display unit connected to the integrated backscatter unit and the image unit for displaying the integrated backscatter IB calculated by the integrated backscatter unit and the B-mode image, the color flow image and/or the M-mode image.

Furthermore, according to a second aspect of the present invention, there is provided ultrasound diagnostic equipment for calculating and displaying scattering coefficients b and n of an organ from received signals, which comprises a tissue power spectrum unit supplied with the received signals for calculating scattering power spectrum of tissues of an object of measurement in the organ, a blood power spectrum unit supplied with the received signals for calculating scattering power spectrum of blood in the organ and estimating blood scattering power spectrum at the portion of the tissues of the object of measurement by using the calculated scattering power spectrum of the blood, a scattering coefficient unit connected to the tissue power spectrum unit and the blood power spectrum unit for normalizing the tissue scattering power spectrum by using the estimated blood scattering power spectrum and for calculating scattering coefficient b and n of the tissues of the object of measurement in the organ by the normalized tissue scattering power spectrum, and a display unit connected to the scattering coefficient unit for displaying the scattering coefficients b and n.

The tissue power spectrum unit may comprise a power spectrum unit supplied with the received signals for calculating scattering power spectrum of the tissues in the organ, and a tissue spatial average unit connected to the power spectrum unit for deriving a spatial average of the scattering power spectra of the tissues in the organ obtained by each scanning line.

The blood power spectrum unit may calculate an average of the blood scattering power spectra for each duration of blood flow speed exceeding threshold levels or for each duration of the blood scattering power exceeding a threshold level, and estimating blood scattering power spectrum at the portion of the tissues of the object of measurement by using the calculated average scattering power spectrum of the blood.

The blood power spectrum unit may comprise a low pass filter having $f^{-n}$ an characteristic, supplied with the received signals, a doppler detector connected to the low pass filter, for calculating a blood flow speed, a blood flow power and scattering power spectrum of the blood, a duration unit connected to the doppler detector for detecting a duration of blood flow speed exceeding threshold levels or a duration of the blood flow power exceeding a threshold level, a correction unit connected to the doppler detector for correcting a variable factor of the blood scattering power spectrum by an individual difference of volume percentage of blood corpuscle in each human, or for correcting the scattering power spectrum of the blood against the blood flow speed, an external designation unit for externally designating a duration where the scattering power spectrum of the blood is calculated, an average unit connected to the duration unit, the correction unit and the external designation unit for averaging the scattering power spectra of the blood in a duration detected by the duration unit or designated by the external designation unit, an interpolation unit connected to the average unit for interpolating optional frequency components of each average scattering power spectrum of blood by an m-th order interpolation, an attenuation correction unit connected to the interpolation unit for correcting blood power spectrum in accordance with attenuation characteristics from the position of the blood to the position of the tissues, and a blood spatial average unit connected to the attenuation correction unit and the scattering coefficient unit for deriving a spatial average of the scattering power spectra of the blood obtained by each scanning line. The doppler detector may include a quadrature detector, an MTI-filter, a flow unit, and a doppler power spectrum unit. The MTI-filter may be applied to a series of data obtained by repeatedly transmitting ultrasound pulses to the same direction, a complex Fourier transformation carried out for data series of output from the MTI-filter for each transmitting, and the blood power spectrum calculated by using results of the complex Fourier transformation. Each frequency component of the blood power spectrum and the tissue power spectrum may be modified so that the number of samples on the frequency axis become the same for each power spectrum.

The scattering coefficient unit may comprise an ROI-setting unit supplied with the received signals for designating an ROI (region of interest) or a marker and for activating a function of moving the ROI or the marker in accordance with a wall-movement, a normalizing unit connected to the tissue power spectrum unit and the blood power spectrum unit for calculating scattering coefficients b and n, and an angle correction unit connected to the normalizing unit for correcting the scattering coefficients b and n according to an angle between a cardiac muscle direction and an ultrasound beam.

The ultrasound diagnostic equipment may further comprise an image unit supplied with the received signals for generating a B-mode image, a color flow image and/or an M-mode image, so that the display unit can display both the scattering coefficients b and n of the tissues and the B-mode image, the color flow image and/or the M-mode image.

The scattering coefficient unit may obtain an oblique line with a linear approximation by applying a method of least squares to the normalized tissue scattering power spectrum, and the scattering coefficient n is determined by a slope of the oblique line and the scattering coefficient b is determined by a crossing point of a Y-axis and the oblique line, where an X-axis is established as logarithmic frequency and the Y-axis is established as decibel expression of the normalized power.

The display unit may display the scattering coefficients b and n of the tissues as a time varying graph. The display unit may display the scattering coefficient b and n of the tissues accompanied with an electrocardiogram. The display unit may display a marker or a color at a duration of blood flow speed exceeding threshold levels or a duration of blood flow power exceeding a threshold level. The display unit may display one-dimensional scattering coefficients b and n profile along a designated direction. The ultrasound diagnostic equipment may be used for diagnosing a myocardial infarction of a heart.

According to the second aspect of the present invention, there is also provided ultrasound diagnostic equipment for calculating and displaying scattering coefficients b and n of an organ from received signals, which comprises a probe, contacted to a body surface over the organ for radiating an ultrasound beam to an optional portion using electrical pulses and receiving ultrasound waves scattered from the optional portion and converting the received ultrasound waves to received electrical signals, a transmitting circuit for generating electrical pulses in accordance with a predetermined timing, a transmitting amplifier connected between the probe and the transmitting circuit for amplifying the electrical pulses and driving the probe, a receiving amplifier connected to the probe for amplifying electrical signals received by the probe, a tissue power spectrum unit connected to the receiving amplifier for calculating scattering power spectrum of a tissue region of an object of measurement in the organ, a blood power spectrum unit connected to the receiving amplifier for calculating scattering power spectrum of a blood region of the object of measurement in the organ, and for estimating blood scattering power spectrum at a portion of the tissue region by using the calculated scattering power spectrum of the blood, a scattering coefficient unit connected to the tissue power spectrum unit and the blood power spectrum unit for normalizing the tissue scattering power spectrum calculated by the tissue power spectrum unit by using the blood scattering power spectrum estimated by the blood power spectrum unit, and for calculating scattering coefficients b and n, an image unit connected to the receiving amplifier, for generating a B-mode image and/or an M-mode image, and a display unit connected to the scattering coefficient unit and the image unit for displaying the scattering coefficients b and n calculated by the scattering coefficient unit and the B-mode image and/or M-mode image generated by the image unit.

BRIEF DESCRIPTION OF THE DRAWINGS

The present invention will be more clearly understood from the description of the preferred embodiments as set forth below with reference to the accompanying drawings, wherein:

FIG. 1 is a block diagram showing a construction of one embodiment according to a first aspect of the present invention;

FIGS. 2A to 2C are diagram for explaining a measuring method of IB;

FIGS. 4A to 4C are a block diagram showing an example of the first aspect of the present invention;

FIGS. 5A to 5E are explanatory diagrams of a blood reference duration and a blood reference portion;

FIGS. 6A to 6E are diagram showing an example for displaying an IB;

FIG. 8 is a block diagram showing a construction of one embodiment according to a second aspect of the present invention;

FIGS. 9A and 9B are diagrams for explaining the concept of the second aspect of the present invention;

FIGS. 11, 11A to 11C are a block diagram showing an example of the second aspect of the present invention;

FIGS. 14A to 14F are diagrams showing an example for displaying scattering coefficients; and FIGS. 15A to 15D are diagrams showing another example for displaying scattering coefficients.

DESCRIPTION OF THE PREFERRED EMBODIMENTS

Figures 3A, 3B:
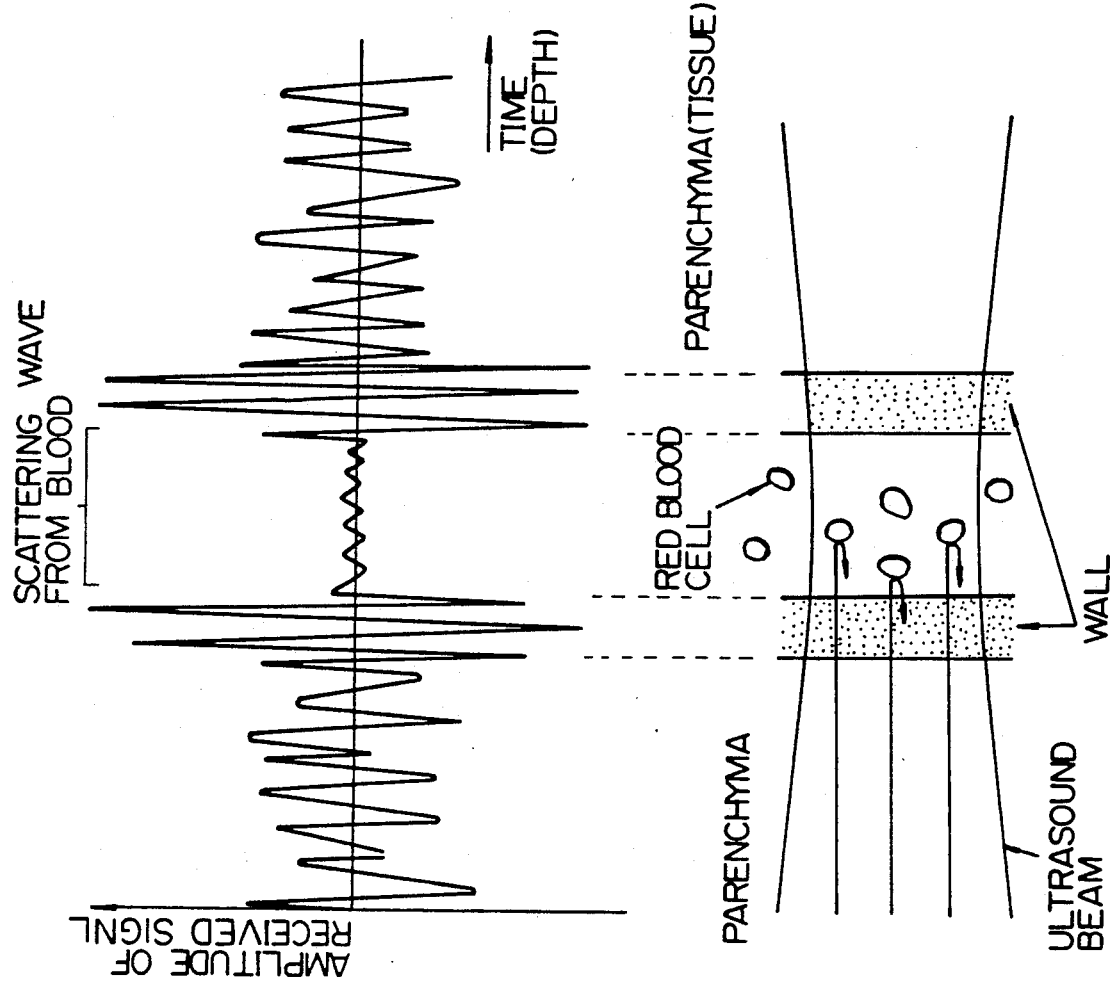
FIGS. 3A and 3B are explanatory diagrams of a blood scattering wave.

Below examples of ultrasound diagnostic equipment according to the present invention will be explained with reference to the drawings.

First, an embodiment of ultrasound diagnostic equipment according to a first aspect of the present invention will be explained with reference to FIGS. 1 to 7D.

FIG. 1 is a block diagram showing a construction of one embodiment according to a first aspect of the present invention. Ultrasound diagnostic equipment of the first aspect of the present invention is used for calculating and displaying an integrated backscatter IB of an organ from received ultrasound signals. The ultrasound diagnostic equipment is, for example, used for diagnosing a myocardial infarction of a heart.

In FIG. 1, scattering power of tissues in an organ (tissue scattering power) at the tissues of an object of measurement (a tissue region B) is calculated by the tissue power unit 5 with using the received ultrasound signal reflected by the tissue region B.

The scattering power of blood in an organ (blood scattering power) at a portion of blood of an object of measurement (a blood region A) is calculated by the blood power unit 6 in accordance with ultrasound signals reflected by the blood region A. The scattering power of blood at the tissue region B is estimated by the blood power unit 6 using the calculated blood scattering power at the blood region A and the attenuation between the blood region A and the tissue region B. Note, the blood has definite ultrasound scattering characteristics, and attenuation characteristics.

The tissue scattering power (scattering power of tissues), which is calculated by the tissue power unit 5, is normalized (divided) by the integrated backscatter unit 7 using blood scattering power at the tissue region B estimated by the blood power unit 6, and an IB is determined by the normalized tissue scattering power.

In FIG. 1, a probe 1 which is contacted to a body surface over an organ, is used for radiating an ultrasound beam 11 to a blood region A and a tissue region B, and for receiving ultrasound waves scattered from the blood region A and the tissue region B.

A transmitting circuit 3 is used for generating electrical pulses in accordance with a predetermined timing.

A transmitting amplifier 2, which is connected between the probe 1 and the transmitting circuit 3, is used for amplifying the electrical pulses and driving the probe 1.

A receiving amplifier 4, which is connected to the probe 1, is used for amplifying electrical signals received by the probe 1.

A tissue power unit 5, which is connected to the receiving amplifier 4, is used for calculating scattering power of the tissue region B of an object of measurement in the organ.

A blood power unit 6, which is connected to the receiving amplifier 4, is used for calculating scattering power of a blood region A of the object of measurement in the organ, and for estimating blood scattering power at the tissue region B by using the calculated scattering power of the blood.

An integrated backscatter unit 7, which is connected to the tissue power unit 5 and the blood power unit 6, is used for normalizing the tissue scattering power calculated by the tissue power unit 5 by using the blood scattering power estimated by the blood power unit 6, and for calculating an integrated backscatter IB.

An image unit 8, which is connected to the receiving amplifier 4, is used for generating a B-mode image, a color flow image (CFI), an M-mode image, and the like.

A display unit 9, which is connected to the integrated backscatter unit 7 and the image unit 8, is used for displaying the IB calculated by the integrated backscatter unit 7 and the B-mode image, the color flow image, the M-mode image, and the like, which are generated by the image unit 8.

A tissue 10 is a tissue (tissues) of an object of measurement of the present embodiment. The tissue region B located in the tissue 10 is a region for calculating the IB. Note, the blood region A is a region of flowing blood whose scattering and attenuation characteristics are already known.

FIGS. 2A to 2C are diagrams for explaining a measuring method of IB (Integrated Backscatter).

As shown in FIG. 2A, an ultrasound beam 11 is radiated from the ultrasound probe 1, scattering power of the blood region A at a depth Z1 where blood exists is calculated, and blood scattering power at a depth Z3 is estimated by the calculated scattering power of the blood region A and the attenuation between the region A and the region B. Further, scattering power of the tissue region B at the depth Z3 is calculated. Note, as shown in FIG. 2A, a wall dividing the blood and the tissues is located at a depth Z2. Next, a process of calculating an IB of the tissues at the depth Z3 by the scattering power of the tissue region B at the depth Z3 and the blood scattering power at the depth Z3 estimated by the scattering power of the blood at the depth Z1 will be explained with reference to equations.

Assuming the frequency characteristics of transmitted ultrasound pulse signals to be I(f), the scattering power of tissues to be $P_T(Z)$, the scattering power of blood to be $P_B(Z)$, the characteristics including transmitting-receiving characteristics of an ultrasound probe and sound field characteristics to be F(f, Z), the round trip attenuation characteristics from the probe 1 to a depth Z to be A(f, Z), and the scattering characteristics of blood to be $b_B f^4$, the blood scattering power at a depth Z1 is indicated by the following equation (1).

$$P_B(Z1) = \int_{-\infty}^{+\infty} I(f)\, F(f, Z1)\, A(f, Z1)\, b_B f^4\, df \quad (1)$$

The blood scattering power at the depth Z3 is approximately assumed to give the following equation from the scattering power of the engine (1).

$$P_B(Z3) = P_B(Z1) \int_{-\infty}^{+\infty} G(f, Z3; Z1)\, A_B(f, Z2; Z1)\, A_T(f, Z3; Z2)\, df \quad (2)$$

Where, G(f, Z3; Z1) indicates a correction term of a sound field change between the depth Z1 and Z3, $A_B$(f, Z2; Z1) indicates attenuation characteristics of blood between the depth Z1 and Z2, and $A_t$(f, Z3; Z2) indicates attenuation characteristics of the tissues between the depth Z2 and Z3.

Therefore, a relationship indicated by the following equation is produced.

$$A(f, Z3) = A(f, Z1) A_B(f, Z2; Z1) A_T(f, Z3; Z2)$$

$$G(f, Z3; Z1) = F(f, Z3)/F(f, Z1)$$

Further, the scattering power of the tissues at the depth Z3 is indicated by the following equation (3).

$$P_T(Z3) = \int_{-\infty}^{+\infty} I(f) F(f, Z3) A(f, Z3) b_T f^n \, df \quad (3)$$

Next, normalizing the equation (3) by the using the equation (2), the following equation (4) is obtained.

$$F(Z3) = P_T(Z3)/P_B(Z3) \quad (4)$$

Note, the equation (4) indicates an integrated backscatter IB of the tissues determined on the basis of the blood scattering power, in the present embodiment.

FIG. 2B is an explanatory graph chart of an IB corresponding to the equation (4) display by the display unit 9. The IB of the present embodiment is obtained by using scattering power of blood, which has a determined value with no individual difference as a standard, and thus the obtained IB has an absolute value. Therefore, the IB of the present embodiment gives two values; an absolute value and a rate of change, compared with the conventional IB's giving only rate of change. This means the IB of the present embodiment gives more information for diagnosis. Namely, the display unit 9 can display the IB of the tissue region B as a graph showing changes over time.

FIG. 2C is an explanatory electrocardiogram which can be incorporated to the graph of IB shown in FIG. 2B by the display unit 9, in order to enhance the timing information.

FIGS. 3A and 3B are explanatory diagrams of a blood scattering wave.

FIG. 3A indicates scattering waves (amplitude of received signal) corresponding to a parenchyma (tissue) and a blood shown in FIG. 3B. As understood from the scattering waves, the scattering power of the blood is much smaller than the scattering power of the tissues. Further, large reflected waves may be frequently returned from the wall and/or the tissues and may overlap on the waves reflected from the blood. Therefore, it is difficult to calculate the scattering power of the blood with high accuracy due to the influence of reflections from the wall and/or the tissues. A blood scattering power can be calculated by using the doppler power of the blood flow obtained by a doppler detector 62 in FIGS. 4, 4A to 4C which will be described below, with decreasing the influence of reflections generated from the wall and/or the tissues.

Figure 4B:
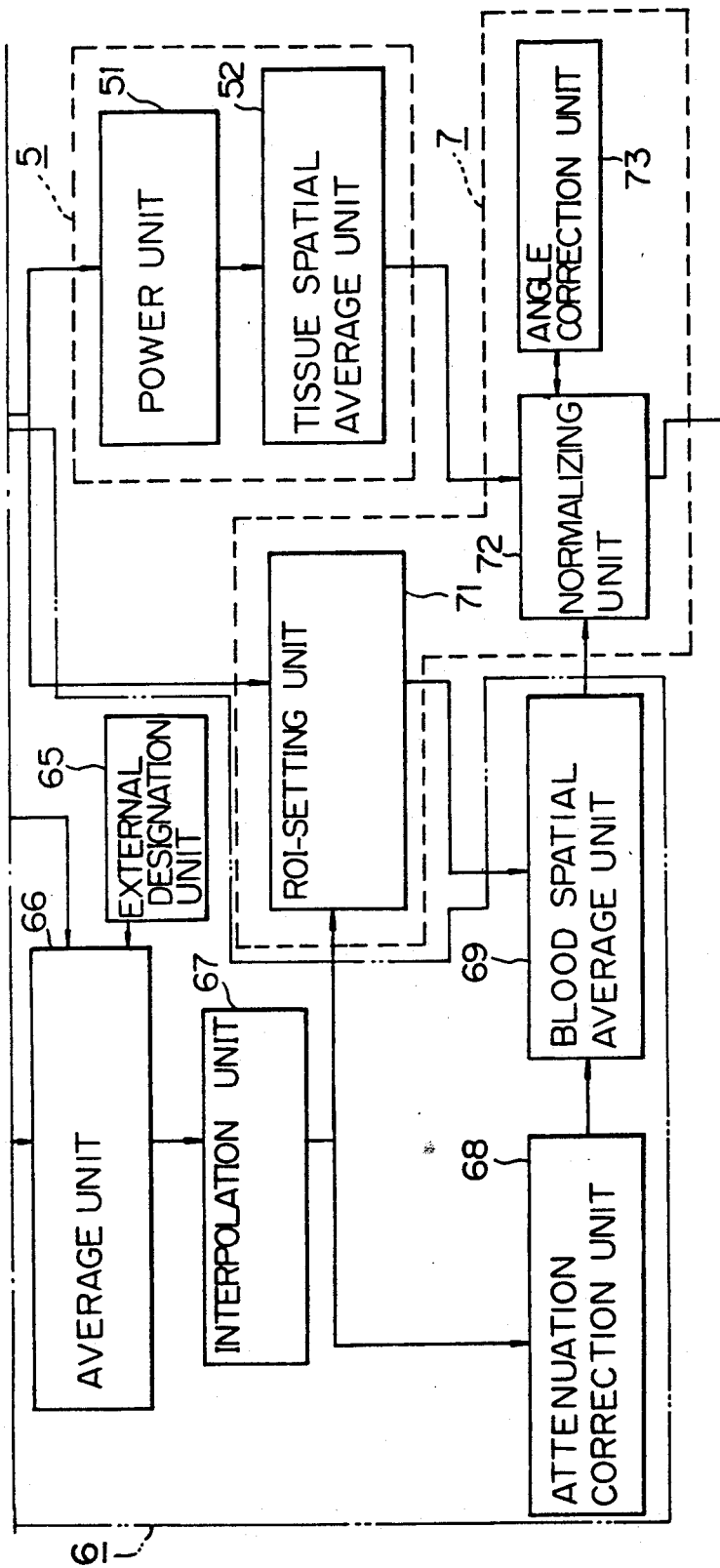
Figure 4C:
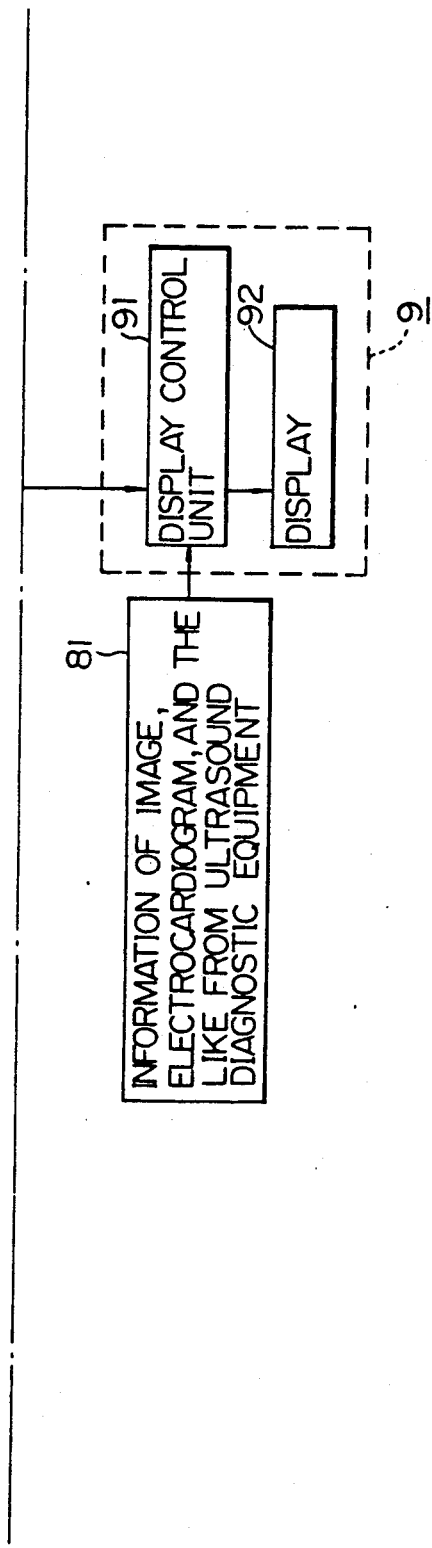

FIGS. 4A to 4C arranged as shown in FIG. 4D are a block diagram showing an example of the present invention.

In FIGS. 4, 4A, 4B and 4C a received signal 41 indicates a signal received by a probe 1.

The tissue power unit 5 is, for example constituted by a power unit 51 and a tissue spatial average unit 52.

The power unit 51, which is supplied with the received signal, is used for calculating scattering power of the tissue region B.

The tissue spatial average unit 52, which is connected to the power unit 51, is used for deriving a spatial average of the scattering powers of the tissue region B obtained by each scanning line.

The blood power unit 6 is for example constituted by a low pass filter 61, a doppler detector 62, a duration unit 63, a correction unit 64, an external designation unit 65, an average unit 66, an interpolation unit 67, an attenuation correction unit 68, and a blood spatial average unit 69.

The low pass filter 61 has $f^{-n}$ characteristics, and is supplied with the received signal. Assuming that scattering strength (or a differential scattering cross section) is $b_S$, it is already known that the scattering characteristics of blood are indicated by $b_B f^4$, and thus a signal having a constant scattering characteristic against frequency can be obtained by passing the signal through a filter having $f^{-4}$ characteristics. Note, the n can be changed to another value.

The doppler detector 62 is constituted by a quadrature detector 621, and MTI-filter 624, a flow unit 622, and a doppler power unit 623, and a blood flow speed and a blood flow power are calculated thereby.

The duration unit 63 is connected to the doppler detector 62, being connected to the flow unit 622 and the doppler power unit 623. The duration unit 63 is used for detecting a duration of the blood flow speed exceeding threshold levels or a duration of the blood flow power exceeding a threshold level (with reference to FIGS. 5C and 5D).

The correction unit 64 is connected to the doppler detector 62, being connected to the doppler power unit 623. The correction unit 64 is used for correcting a variable factor of the blood scattering power by an individual difference of volume percentage of blood corpuscle in each human, or for correcting the scattering power of the blood against the blood flow speed.

The external designation unit 65 is used for externally designating a duration where the blood scattering power is calculated.

The average unit 66, which is connected to the duration unit 63, the correction unit 64 and the external designation unit 65, is used for averaging the scattering power of the blood in a duration detected by the duration unit 63 or designated by the external designation unit 65.

The interpolation unit 67, which is connected to the average unit 66, is used for interpolating each average scattering power of the blood by an m-th order interpolation (with reference to FIG. 5E), when scattering power cannot be sufficiently obtained for the reason that the blood flow speed is too slow. Note, in FIG. 5E, the interpolation is a first-order interpolation.

The attenuation correction unit 68, which is connected to the interpolation unit 67, is used for correcting blood power in accordance with attenuation from the blood region A to the tissue region B.

The blood spatial average unit 69, which is connected to the attenuation correction unit 68 and the integrated backscatter unit 7 (an ROI-setting unit 71), is used for deriving a spatial average of the scattering powers of the blood obtained by each scanning line.

The integrated backscattering unit 7 is, for example, constituted by an ROI-setting unit 71 a normalizing unit 72, and an angle correction unit 73.

The ROI-setting unit 71, which is supplied with the received signal, is used for designating an ROI (region of interest) or a marker, and for activating a function of moving the ROI or the marker in accordance with a well-movement.

The normalizing unit 72, which is connected to the tissue power unit 5 (the tissue spatial average unit 52) and the blood power unit 6 (the blood spatial average unit 69), is used for calculating an integrated backscatter IB according to, for example, the equation (4).

The angle correction unit 73, which is connected to the normalizing unit 72, is used for correcting the integrated backscatter IB according to an angle between a cardiac muscle direction and the ultrasound beam 11. More detailed explanation of this correction operation is given later with reference to FIG. 7.

A reference numeral 81 denotes information of an image, an electrocardiogram, and the like from the ultrasound diagnostic equipment.

A reference numeral 91 denotes a display control unit for controlling a display 92, which is connected to the integrated backscatter unit 7 (the normalizing unit 72) and is supplied with the information 81.

FIGS. 5A to 5E are explanatory diagrams of a blood reference duration, and a blood reference portion and a tissue reference portion.

Figure 5A:
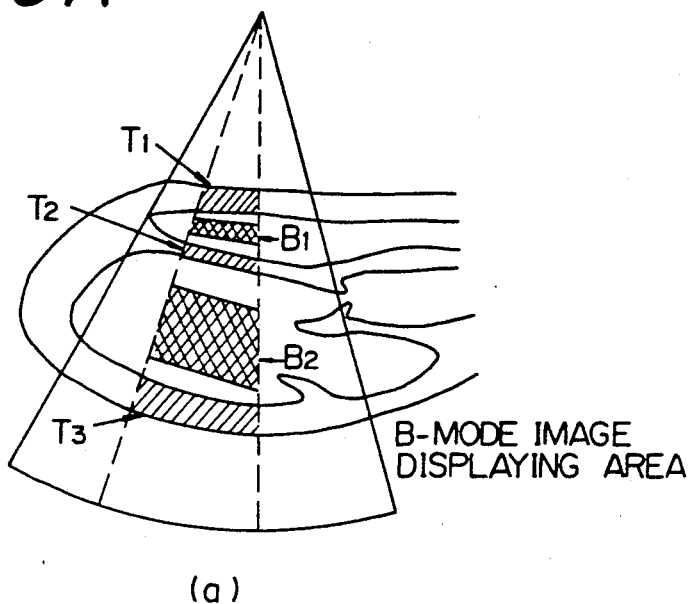

FIG. 5A indicates a B-mode image display area, calculable regions (B1, B2) of blood power, and detectable regions (T1, T2, T3) of tissues.

Figure 5B:
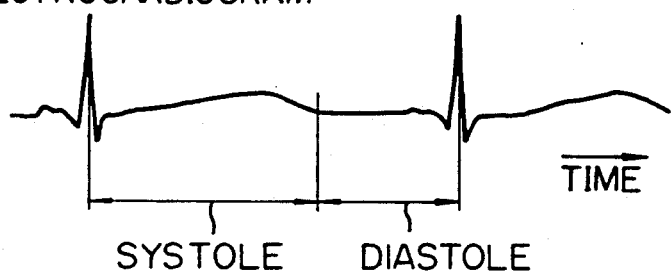

FIG. 5B indicates an electrocardiogram.

FIG. 5C indicates blood scattering power and durations of the blood power exceeding a specific threshold level with added markers.

FIG. 5D indicates blood flow speed and durations of the blood flow speed (velocity) exceeding specific threshold levels with added markers. Namely, the display unit 9 can display a marker or a color at a duration of a blood flow speed's exceeding threshold levels or a duration of a blood flow power's exceeding a threshold level.

FIG. 5E indicates the scattering power interpolated by a first-order interpolation, which is shown by a dot-line in FIG. 5E. The integrated backscatter IB of the tissues for all durations can be obtained by using the above interpolation.

Figure 6A:
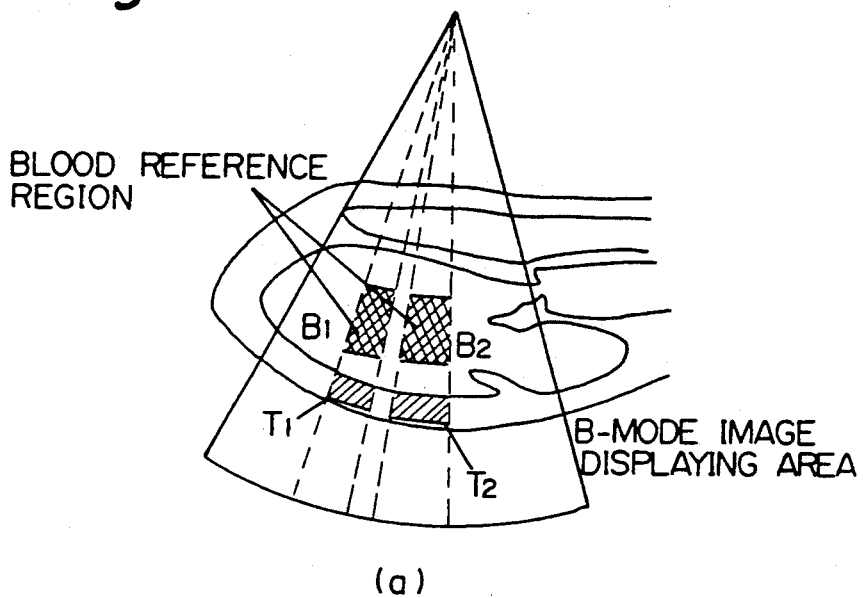
Figure 6B:
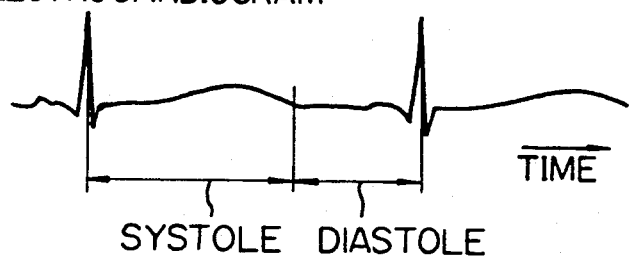

FIGS. 6A and 6B are diagrams showing an example of displaying an IB.

FIG. 6A indicates calculation portions of an IB of tissues T1 and T2, and blood reference regions B1 and B2 by using a display area of a B-mode image.

FIG. 6B indicates an electrocardiogram.

FIG. 6C indicates examples of time varying graph of the IB of the tissues T1 and T2.

FIG. 6D indicates a marker in a blood reference time phase.

FIG. 6E indicates an example of a color coded image of an IB superimposed on an M-mode image. Note, FIGS. 6A to 6E can be voluntarily indicated on the display unit in any combination.

FIGS. 7A to 7D are diagrams showing an example of displaying an IB.

Figure 7A:
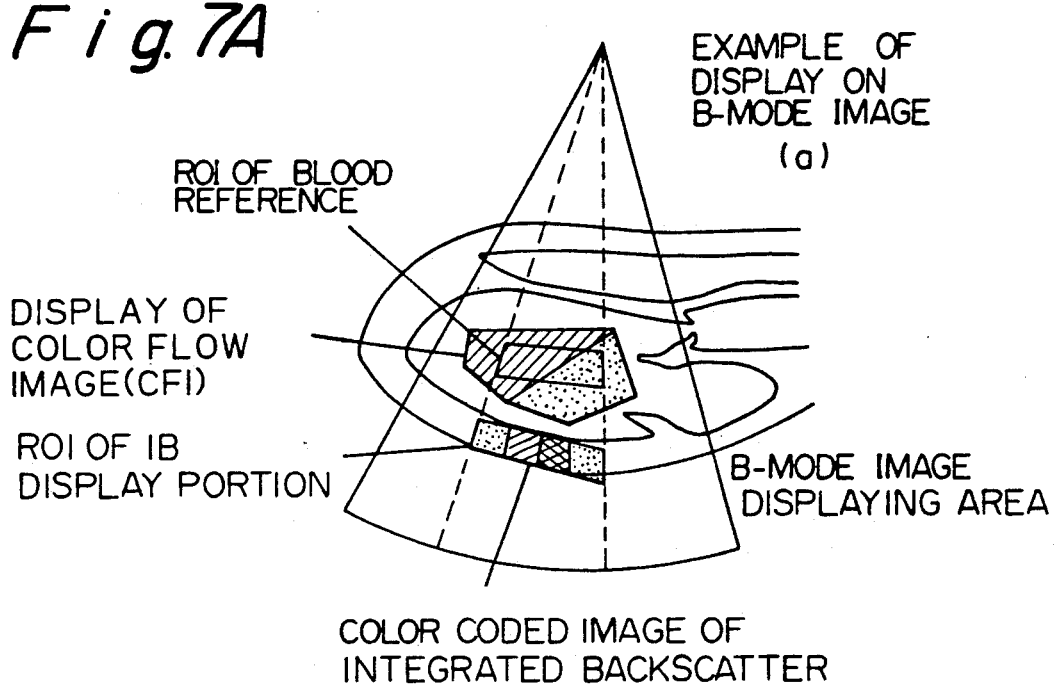
FIGS. 7A to 7D are diagram showing another example for displaying an IB.

FIG. 7A indicates an IB, which is indicated by a color indication, on a B-mode image with a well-known color flow image (CFI). Furthermore, an ROI for indicating a region, where the blood power is calculated, is also indicated. In this diagram, the color flow image and the IB are simultaneously indicated, but it can be constituted so that the color flow image and the IB are separately indicated by different displays, or only the IB is indicated.

Figure 7B:
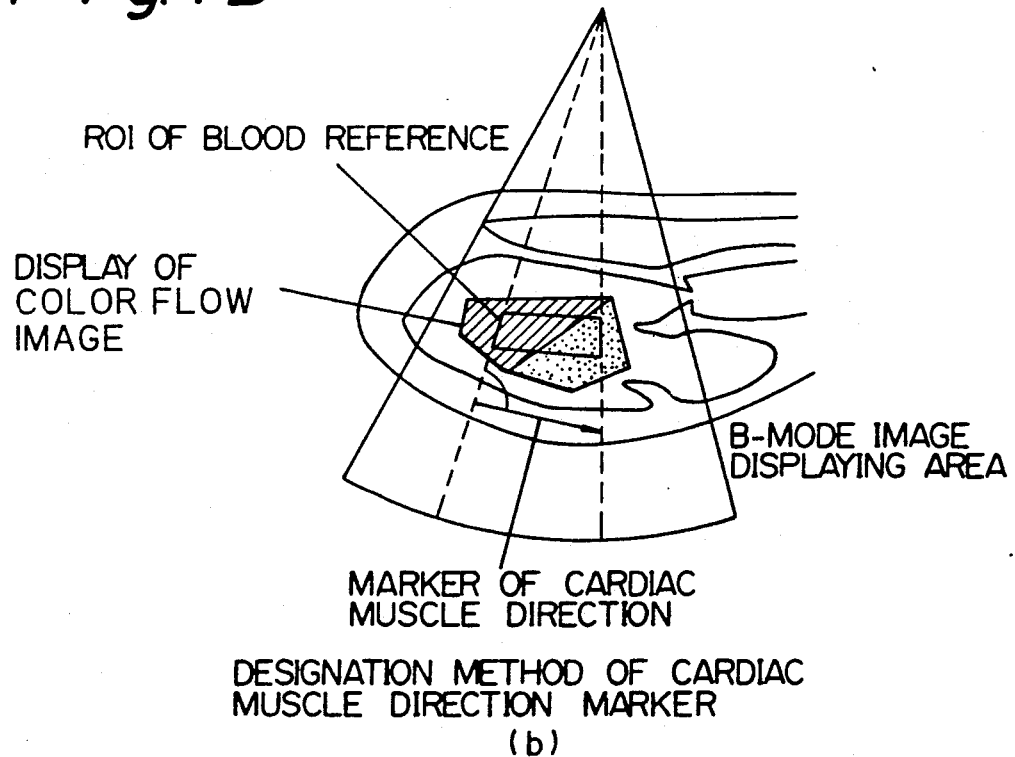
Figure 7C:
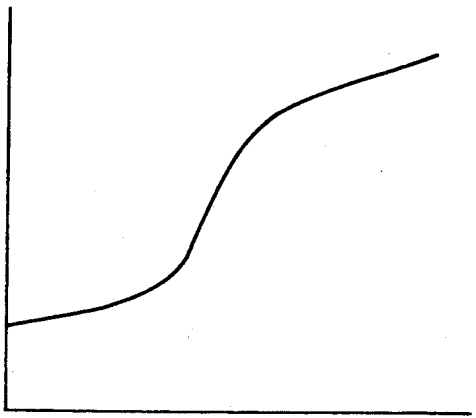

FIG. 7B indicates a marker which is externally established at the state of freezing of the B-mode image or the color flow image to indicate a cardiac muscle direction. Note, it is well known that the integrated backscatter IB varies depending on an angle between a scanning direction and the muscle. FIG. 7C indicates an example of the factor to correct the angle dependency.

Figure 7D:
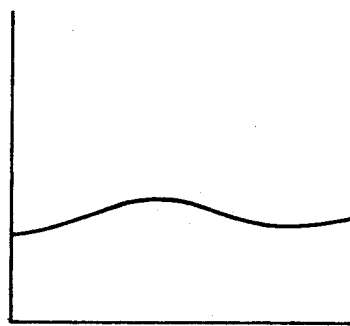

FIG. 7D indicates an explanatory example of one-dimensional profile of an integrated backscatter IB of the tissues with reference to blood. Namely, the display unit 9 can display a spatial IB of the tissues as a profile.

According to the first aspect of the present invention as in the above descriptions, blood scattering power at a portion of tissues of an object of measurement is estimated by using a scattering power of blood which has definite ultrasound scattering characteristics, scattering power of the tissues of the object of measurement is normalized (divided) by the estimated scattering power of the blood, and an integrated backscatter IB is obtained and displayed, so that the IB of the tissues can be quantitatively estimated without being influenced by attenuation.

Furthermore, this estimated quantitative IB of the tissues is displayed on the display unit accompanied with a B-mode image, an electrocardiogram, and the like, so that diagnostic accuracy can be increased.

Next, an embodiment of ultrasound diagnostic equipment according to a second aspect of the present invention will be explained with reference to FIGS. 8 to 15D.

FIG. 8 is a block diagram showing a construction of one embodiment according to a second aspect of the present invention. Ultrasound diagnostic equipment of the second aspect of the present invention is used for calculating and displaying scattering coefficients b and n of an organ from received ultrasound signals. The ultrasound diagnostic equipment is, for example, used for diagnosing a myocardial infarction of a heart. Note, the scattering coefficients b and n are defined in the following equation.

$$S(f) = b f^n$$

In FIG. 8, a tissue power spectrum unit 5a is used for calculating scattering power spectrum of tissues of an object of measurement in an organ. A blood power spectrum unit 6a is used for calculating scattering power spectrum of blood in the organ and estimating blood scattering power spectrum at a portion of the tissues of the object of measurement by using the calculated scattering power spectrum of the blood and the attenuation characteristics between a blood region A and a tissue region B. A scattering coefficient unit 7a is used for normalizing the tissue scattering power by using the estimated blood scattering power spectrum, and for calculating scattering coefficients b and n by the normalized tissue scattering power spectrum.

As shown in FIG. 8, scattering power spectrum of tissues in an organ (tissue scattering power spectrum) at the tissues of an object of measurement (a tissue region B) is calculated by the tissue power spectrum unit 5a by using the received ultrasound signal reflected by the tissue region B.

The scattering power spectrum of blood in an organ (blood scattering power spectrum) at a portion of blood of an object of measurement (a blood region A) is calculated by the blood power spectrum unit 6a by using ultrasound signals reflected by the blood region A. The scattering power of blood at the tissue region B is estimated by the blood power spectrum unit 6a by using the calculated blood scattering power spectrum at the blood region A and the attenuation characteristics between the blood region A and the tissue region B. Note, the blood has definite ultrasound scattering and attenuation characteristics.

The tissue scattering power spectrum (scattering power spectrum of tissues), which is calculated by the tissue power spectrum unit 5a, is normalized (divided) by the scattering coefficient unit 7a with using blood scattering power spectrum at the tissue region B estimated by the blood power spectrum unit 6a, and scattering coefficients b and n are determined by the normalized tissue scattering power spectrum.

In FIG. 8, the same constituents as in FIG. 1 will have the same name and reference numeral as in FIG. 1, and the explanation thereof will be omitted.

A tissue power spectrum unit 5a, which is connected to the receiving amplifier 4, is used for calculating scattering power spectrum of the tissue region B of an object of measurement in the organ.

A blood power spectrum unit 6a, which is connected to the receiving amplifier 4, is used for calculating scattering power spectrum of the blood region A of the object of measurement in the organ, and for estimating blood scattering power spectrum at the tissue region B by using the calculated scattering power spectrum of the blood.

A scattering coefficient unit 7a, which is connected to the tissue power spectrum unit 5a and the blood power spectrum unit 6a, is used for normalizing the tissue scattering power spectrum calculated by the tissue power spectrum unit 5a by using the blood scattering power spectrum estimated by the blood power spectrum unit 6a, and for calculating scattering coefficients b and n. Note, the scattering coefficient n is, for example, determined by a slope of the normalized spectrum, and the scattering coefficient b is, for example, determined by a crossing point of a Y-axis and the normalized spectrum (with reference to FIG. 9B). Note, an X-axis is established as logarithmic frequency and the Y-axis is established as decibel expression of the normalized power as shown in FIG. 9B.

A display unit 9, which is connected to the scattering coefficient unit 7a and the image unit 8, is used for displaying the scattering coefficients b and n calculated by the scattering coefficient unit 7a and the B-mode image, the color flow image (CFI), the M-mode image, and the like, which are generated by the image unit 8.

A tissue 10 is a tissue (tissues) of an object of measurement of the present embodiment. The tissue region B located in the tissue 10 is a region for calculating the scattering coefficients. Note, the blood region A is a region of flowing blood whose scattering and attenuation characteristics are already known.

FIGS. 9A and 9B are diagrams for explaining the concept of the second aspect of the present invention.

As shown in FIG. 9A, an ultrasound beam 11 is radiated from the probe 1, the scattering power spectrum of the blood region A at a depth Z1 where blood exists is calculated, and the blood scattering power spectrum at a depth Z3 is estimated by the calculated scattering power spectrum of the blood region A and the attenuation characteristics between the blood region A and the tissue region B. Further, the scattering power spectrum of the tissue region B at the depth Z3 is calculated. Note, as shown in FIG. 9A, a wall dividing the blood and the tissues is located at a dept Z2. Next, a process of calculating scattering coefficients b and n of the tissues at the depth Z3 by the scattering power spectrum of the tissue region B at the depth Z3 and the blood scattering power spectrum at the depth Z3 estimated by the scattering power spectrum of the blood at the depth Z1, will be explained with reference to equations.

Assuming the frequency characteristics of transmitted ultrasound pulse signals to be I(f), the scattering power spectrum of tissues to be $S_T(f, Z)$, the scattering power spectrum of blood to be $S_B(f, Z)$, the characteristics including transmitting-receiving characteristics of a probe and sound field characteristics to be F(f, Z), the round trip attenuation characteristics from the probe 1 to a depth Z to be A(f, Z), and the scattering characteristics of blood to be $b_B f^4$, the blood scattering power spectrum at a depth Z1 is indicated by the following equation (5).

$$S_B(f, Z1) = I(f) \, F(f, Z1) \, A(f, Z1) \, b_B f^4 \quad (5)$$

The scattering power spectrum at the depth Z3 is assumed to give the following equation (6) from the scattering power spectrum of the equation (5).

$$S_B(f, Z3) = G(f, Z3; Z1) \, A_B(f, Z2; Z1) \, A_T(f, Z3; Z2) \, S_B(f, Z1) \quad (6)$$

Where, G(f, Z3, Z1) indicates a correction term of a sound field change between the depth Z1 and Z3, $A_B$(f, Z2; Z1) indicates attenuation characteristics of blood between the depth Z1 and Z2, and $A_T$(f, Z3; Z2) indicates attenuation characteristics of the tissues between the depth Z2 and Z3. Note, $A_T$(f, Z3; Z2) is unknown, so we assume it to have specific characteristics.

Further, the scattering power spectrum of the tissues at the depth Z3 is indicated by the following equation (7).

$$S_T(f, Z3) = I(f) \, F(f, Z3) \, A(f, Z3) \, b_T f^n \quad (7)$$

Where $$A(f, Z3) = A(f, Z1) \, A_B(f, Z2; Z1) \, A_T(f, Z3; Z2)$$

$$G(f, Z3; Z1) = F(f, Z3)/F(f, Z1)$$

Therefore, normalizing the equation (7) by using the equation (6), the following equation (8) is obtained.

$$\begin{aligned} S(f, Z3) &= S_T(f, Z3)/(S_B(f, Z3) \cdot f^{-4}) \\ &= b_T/b_B \cdot f^n \end{aligned} \quad (8)$$

The equation (8) is indicated by the following decibel expression equation (9).

$$10 \log_{10} S(f, Z3) = 10 \log_{10}(b_T/b_B) + 10 \log_{10} f \cdot n \quad (9)$$

A graph indicating the equation (9) is shown in FIG. 9B. Note, an oblique line is obtained with a linear approximation by applying a method of least squares to the normalized scattering power spectrum $10 \log_{10} S(f, Z3)$, and a scattering coefficient n is, for example, determined by a slope of the oblique line and a scattering coefficient b ($=b_T/b_B$) is determined by a crossing point of a Y-axis and the oblique line as shown in FIG. 9B. Namely, the scattering coefficient unit 7a can obtain an oblique line with a linear approximation by applying a method of least squares to the normalized tissue scattering power spectrum, and the scattering coefficient n is determined by a slope of the oblique line and the scattering coefficient b is determined by a crossing point of a Y-axis and the oblique line. Note, an X-axis is established as logarithmic frequency and the Y-axis is established as decibel expression of the normalized power as described above with reference to FIG. 9B.

Therefore, according to the present embodiment, scattering power spectrum of a blood region A at a depth Z1 is calculated, the blood scattering power spectrum at a depth Z3 is estimated, the tissue scattering power spectrum of a tissue region B at the depth Z3 is calculated, the tissue scattering power spectrum of the tissue region B is normalized using the estimated blood scattering power spectrum, a graph of the equation (9) is made, and then a scattering coefficient n is determined by a slope of the oblique line and a scattering coefficient b is determined by a crossing point of a Y-axis.

Figure 10A:
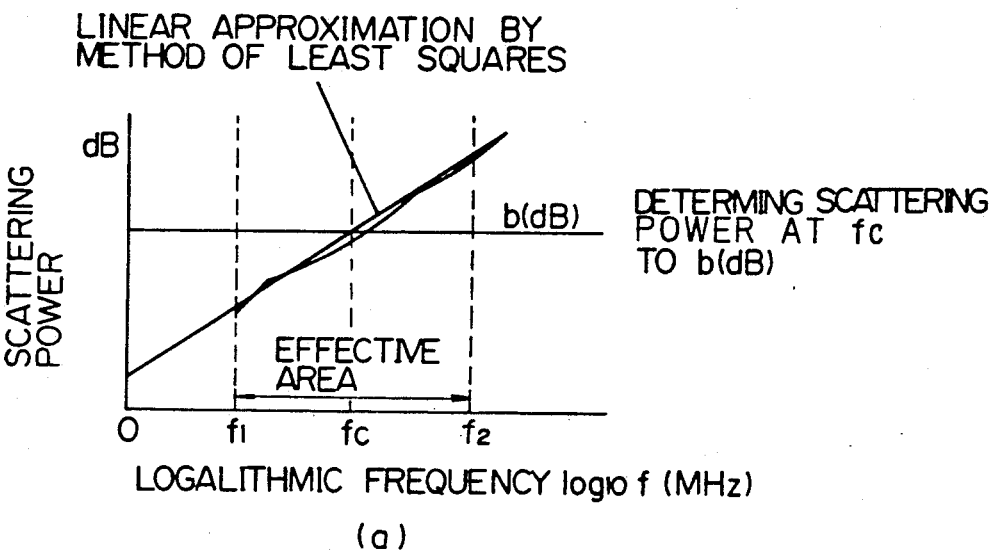
FIGS. 10A and 10B are explanatory diagrams of estimating a scattering strength.
Figure 10B:
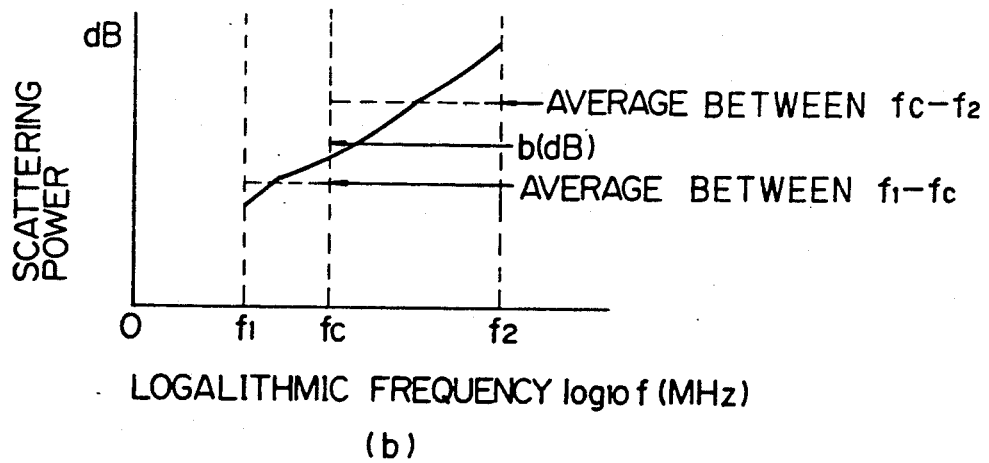

FIGS. 10A and 10B are explanatory diagrams of estimating scattering coefficients (scattering strength) from the normalized scattering power spectrum 10 $\log_{10} S(f, Z3)$.

FIG. 10A indicates an approach, wherein an oblique line is obtained with a linear approximation by applying a method of least squares to a normalized scattering power spectrum between an effective band ($f_1 - f_2$), and a scattering strength b at a center frequency $f_c$ of the effective band (which is a central portion between $f_1$ and $f_2$ on a logarithmic frequency axis). According to this approach, an estimated value b can be obtained with only a small fluctuation.

FIG. 10B indicates another approach, wherein an average power between $f_1$ and $f_c$ and an average power between $f_c$ and $f_2$ are calculated, and a scattering strength b is determined by the following equation (10).

$$\text{Scattering strength } b \text{ at } f_c = [(\text{average power between } f_1 - f_c) + (\text{average power between } f_c - f_2)]/2 \quad (10)$$

FIGS. 3A and 3B, which are used for explaining an embodiment of the first aspect of the present invention, are an explanatory diagrams of a blood scattering wave.

FIG. 3A indicates scattering waves (amplitude of received signal) corresponding to a parenchyma (tissue) and a blood shown in FIG. 3B. As understood from the scattering waves, the scattering power of the blood is much smaller than the scattering power of the tissues. Further, large reflected waves may be frequently returned from the wall and/or the tissues and may overlap on the waves reflected from the blood. Therefore, it is difficult to calculate the scattering power of the blood with high accuracy due to the influence of reflections from the wall and/or the tissues. These multiple reflections can be removed from the scattering power spectrum of the blood by a doppler detector 62a in FIGS. 11A to 11C, which will be described below.

Figure 11B:
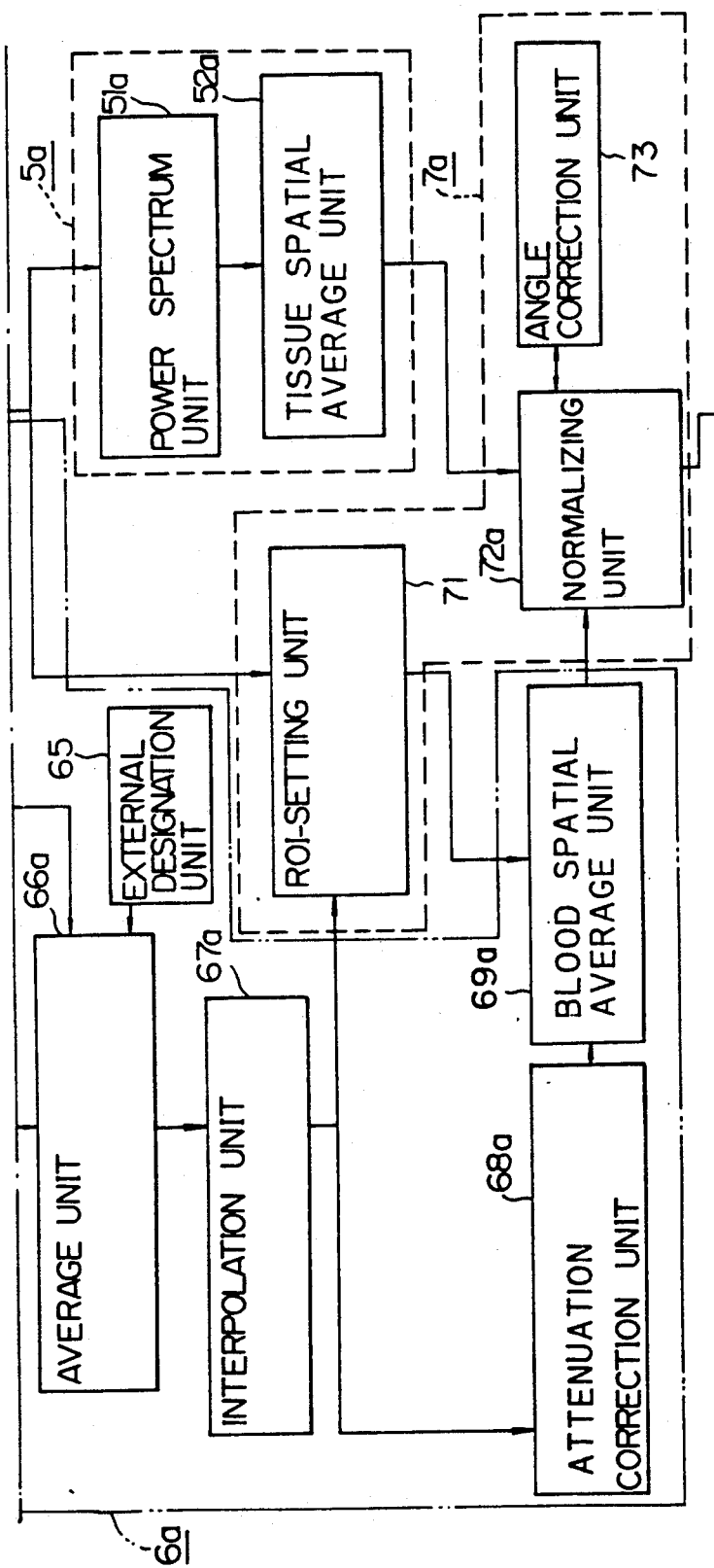
Figure 11C:
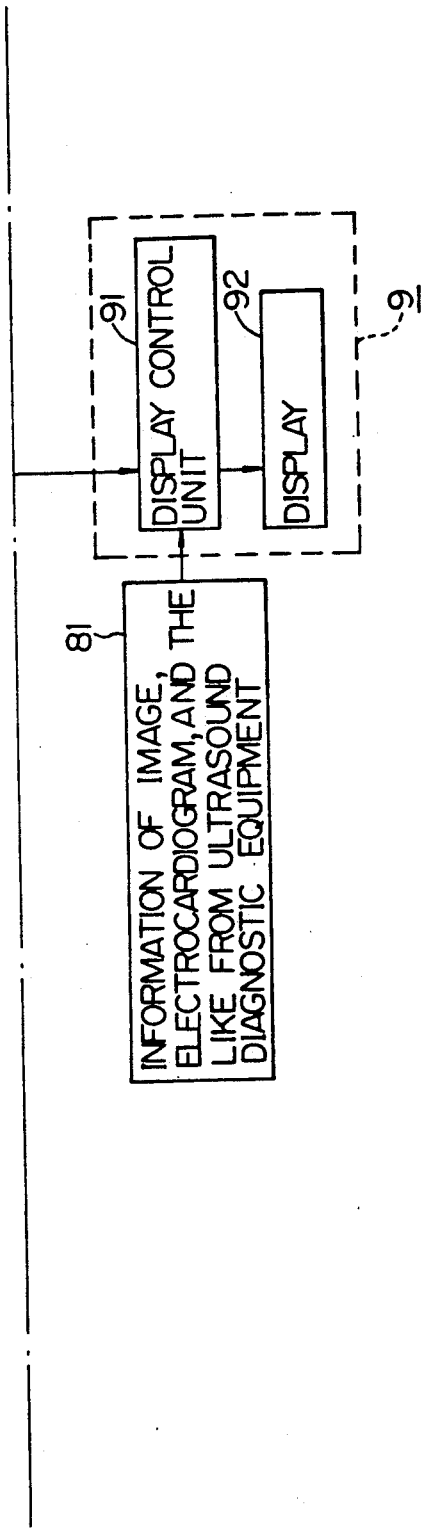

FIGS. 11A to 11C, arranged as shown in FIG. 11, are a block diagram showing an example of the second aspect of the present invention.

In FIGS. 11A, 11B and 11C, a received signal 41 indicates a signal received by a probe 1.

The tissue power spectrum unit 5a is, for example, constituted by a power spectrum unit 51a and a tissue spatial average unit 52a.

The power spectrum unit 51a, which is supplied with the received signal, is used for calculating scattering power spectrum of the tissue region B.

The tissue spatial average unit 52a, which is connected to the power spectrum unit 51a, is used for deriving a spatial average of the scattering power spectrum of the tissue region B obtained by each scanning line.

The blood power spectrum unit 6a is, for example, constituted by a low pass filter 61, a doppler detector 62a, a duration unit 63, a correction unit 64a, an external designation unit 65, an average unit 66a, an interpolation unit 67a, an attenuation correction unit 68a, and a blood spatial average unit 69a.

The low pass filter 61 is the same as in FIG. 4.

The doppler detector 62a is constituted by a quadrature detector 621, an MTI-filter 624, a flow unit 622, and a doppler power spectrum unit 623a and the like, and a speed, scattering power spectrum and scattering power of the blood are calculated thereby.

The duration unit 63 is connected to the doppler detector 62a, or connected to the flow unit 622 and the doppler power spectrum unit 623a. The duration unit 63 is used for detecting a duration of the blood flow speed exceeding threshold levels or a duration of the blood flow power exceeding a threshold level (with reference to FIGS. 13C and 13D).

The correction unit 64a is connected to the doppler detector 62a, or connected to the doppler power spectrum unit 623a. The correction unit 64a is used for correcting a variable factor of the blood scattering power spectrum by an individual difference of volume percentage of blood corpuscle in each human, or for correcting the scattering power spectrum of the blood against the blood flow speed.

The external designation unit 65 is used for externally designating a duration where the blood scattering power spectrum is calculated.

The average unit 66a, which is connected to the duration unit 63, the correction unit 64a and the external designation unit 65, is used for averaging the scattering power spectrum of the blood in a duration detected by the duration unit 63 or designated by the external designation unit 65.

The interpolation unit 67a, which is connected to the average unit 66a, is used for interpolating scattering power spectrum of blood by an m-th order interpolation (with reference to FIG. 13E), when scattering power spectrum cannot be sufficiently obtained for the reason that the blood flow speed is too slow. Note, in FIG. 13E, the interpolation is a first-order interpolation.

The attenuation correction unit 68a, which is connected to the interpolation unit 67a, is used for correcting blood power spectrum in accordance with attenuation characteristics between the blood region A and the tissue region B.

The blood spatial average unit 69a, which is connected to the attenuation correction unit 68a and the scattering coefficient unit 7a (an ROI-setting unit 71), is used for deriving a spatial average of the scattering power spectra of the blood obtained by each scanning line.

The scattering coefficient unit 7a is, for example, constituted by an ROI-setting unit 71, a normalizing unit 72a, and an angle correction unit 73.

The ROI-setting unit 71, which is supplied with the received signal, is used for designating an ROI or a marker, and for activating a function of moving the ROI or the marker in accordance with a wall-movement.

The normalizing unit 72a, which is connected to the tissue power spectrum unit 5a (the tissue spatial average unit 52a) and the blood power spectrum unit 6a (the blood spatial average unit 69a), is used for calculating scattering coefficients b and n.

The angle correction unit 73, which is connected to the normalizing unit 72a, is used for correcting the scattering coefficients b and n according to an angle between a cardiac muscle direction and the ultrasound beam 11.

A reference numeral 81 denotes information of an image, an electrocardiogram, and the like from the ultrasound diagnostic equipment.

A reference numeral 91 denotes a display control unit for controlling a display 92, which is connected to the scattering coefficient unit 7a (the normalizing unit 72a) and is supplied with the information 81.

Figure 12A:
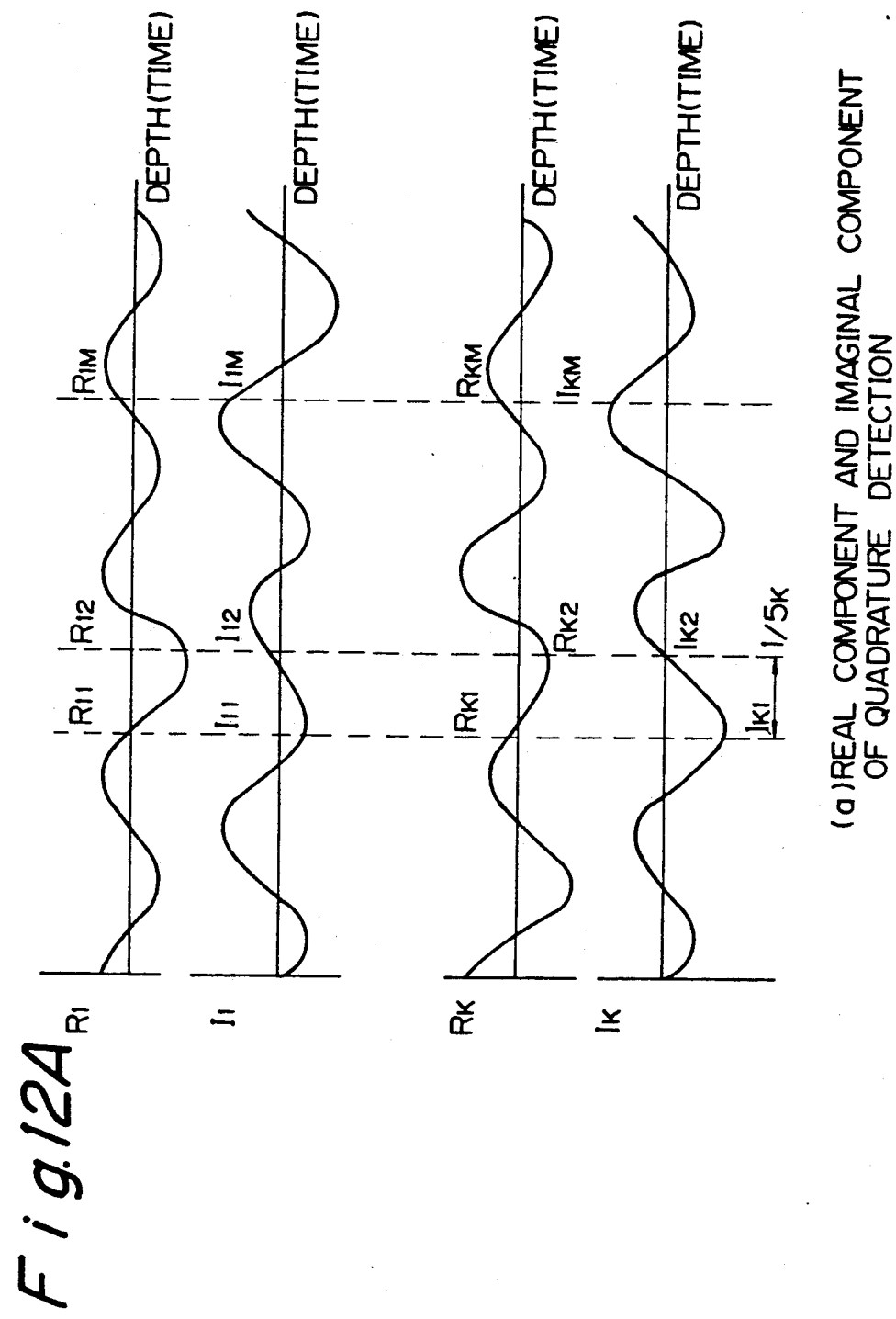
FIGS. 12A to 12E are diagrams for explaining a comparison method between blood scattering power spectrum and tissue scattering power spectrum.
Figure 12B:
Figure 12C:
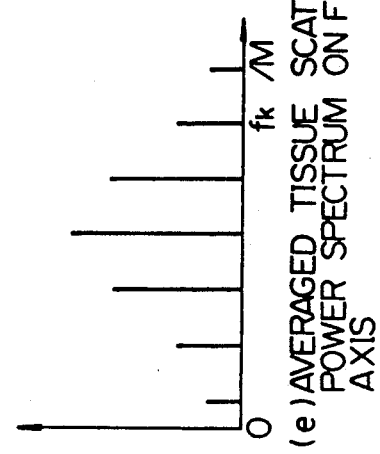
Figure 12D:
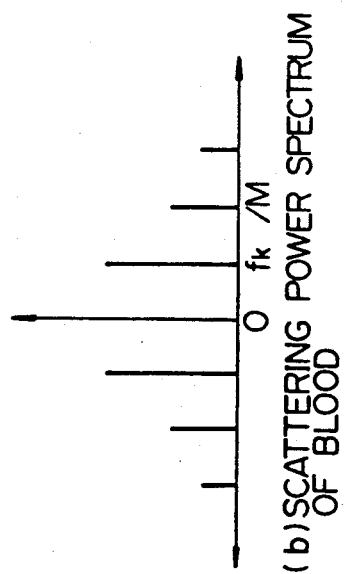
Figure 12E:
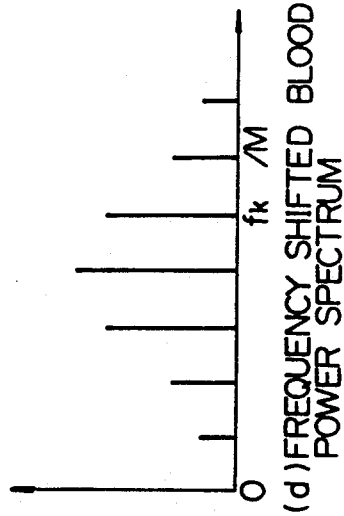

FIGS. 12A and 12E are diagrams for explaining a method to compare a blood scattering power spectrum with tissue scattering power spectrum.

FIG. 12A indicates real components and imaginary components after a quadrature detection. Namely, FIG. 12A indicates two output waveforms as examples of output waveforms in a quadrature detector 621. When estimating a blood flow speed and the like by using the quadrature detector 621, K ultrasound pulses are transmitted in the same scanning line direction. A reference I denotes an imaginary component, and a reference R denotes a real component. Below, a calculation of the scattering power spectrum of blood flow using the quadrature detector will be explained.

First, in order to remove influence from a slow wall-signal or a reflected signal of a parencyma, a well-known MTI-filter is applied to a series of data sampled at the same depth. Namely, the MTI-filter is applied to a series of data $(R_{1j}, R_{2j}, \ldots R_{kj}), I_{1j}, I_{2j}, \ldots I_{kj})$; $(j=1, 2, \ldots M)$, which are obtained by repeatedly transmitting ultrasound pulses and sampling the output of the quadrature detector at the timing corresponding to the same depth, and then the power spectrum is calculated by carrying out a complex Fourier transformation on the data series $R_{ij}, I_{ij}$, (where, $j=1$ to M). FIG. 12B indicates an average power spectrum which is related to i as described above. Note, the power spectrum of the tissues can be obtained by carrying out a Fourier transformation on the reflected signal. FIG. 12C indicates estimated power spectrum of the tissues for data acquisition duration T with a sampling frequency $f_s$.

FIG. 12D indicates blood power spectrum obtained by shifting the power spectrum of the blood as shown in FIG. 12B by a value corresponding to a mixing frequency. FIG. 12E indicates blood power spectrum obtained by averaging power spectrum of the tissues of FIG. 12C by $N_{sx}$ pieces on a frequency axis, where, $$N_{sx}=(f_k/M)/(f_s/T) \tag{11}$$

Note, scattering coefficients can be obtained by comparing FIGS. 12D and 12E.

Figure 13A:
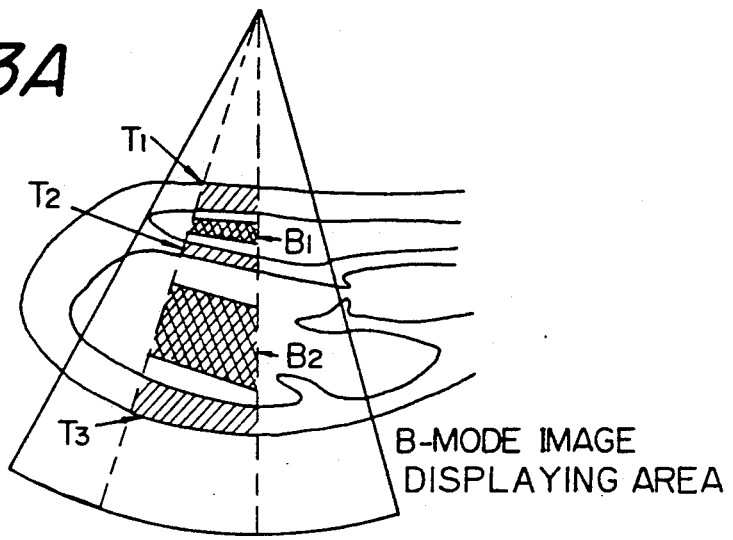
FIGS. 13A to 13E are explanatory diagrams of a blood reference duration and a blood reference portion.
Figure 13B:
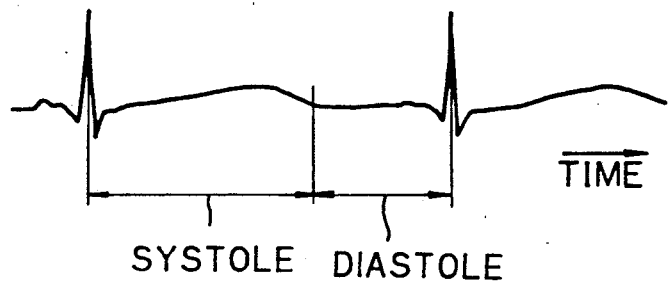
Figures 13C, 13D, 13E:
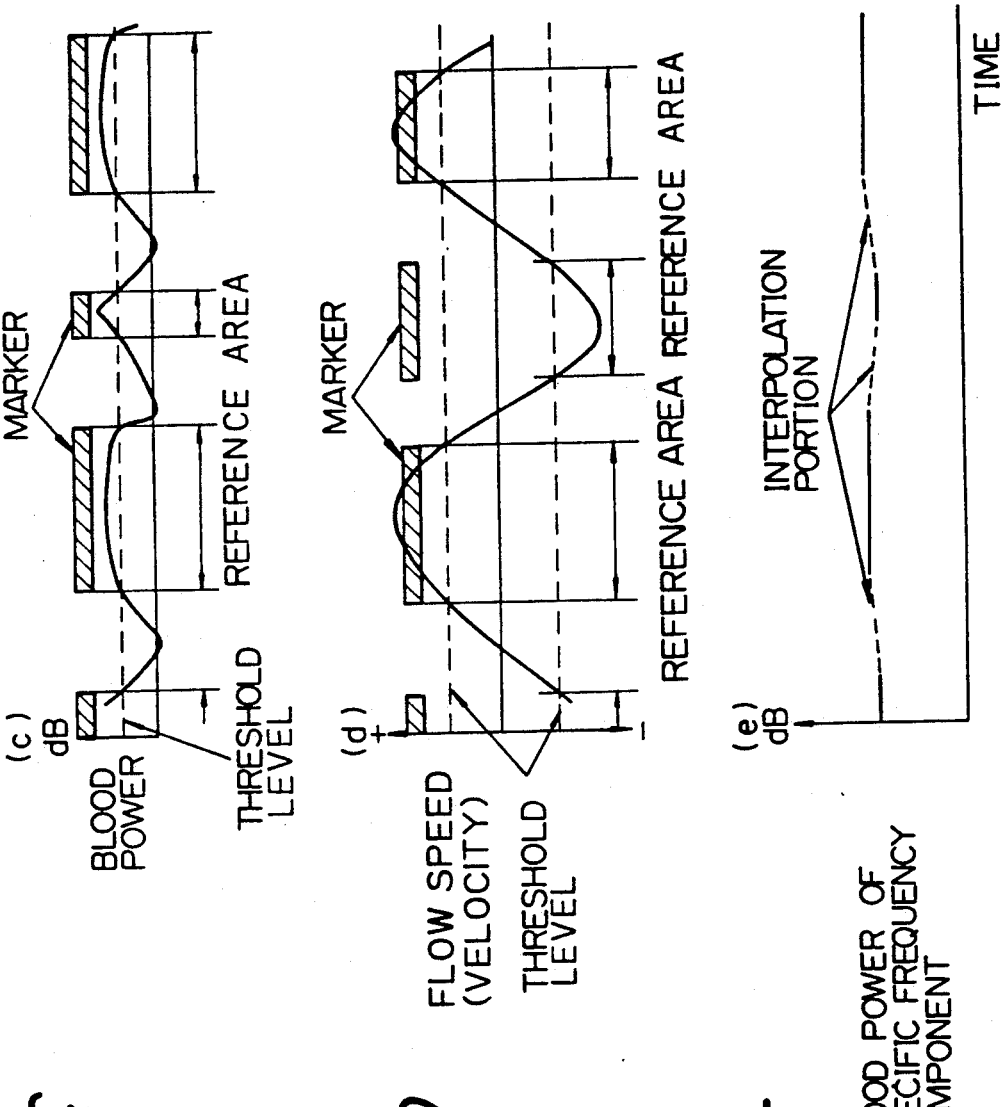

FIGS. 13A and 13E are explanatory diagrams of a blood reference duration, a blood reference portion and a tissue reference portion.

FIG. 13A indicates a B-mode image display area, calculable regions (B1, B2) of blood power spectrum, and detectable regions (T1, T2, T3) of tissues.

FIG. 13B indicates an electrocardiogram.

FIG. 13C indicates blood scattering power and durations of the blood power exceeding a specific threshold level with added markers.

FIG. 13D indicates blood flow speed and durations of the blood flow speed (velocity) exceeding specific threshold levels with added markers. Namely, the display unit 9 can display a marker or a color at a duration of a blood flow speed exceeding threshold levels or duration of a blood flow power exceeding a threshold level.

FIG. 13E indicates a specific frequency component of the scattering power spectrum interpolated by a first-order interpolation, which is shown by a dot-line in FIG. 13E. The scattering coefficients of the tissues in all durations can be obtained by using the above interpolated power spectra.

FIGS. 14A to 14F are diagrams showing an example for displaying scattering coefficients.

Figure 14A:
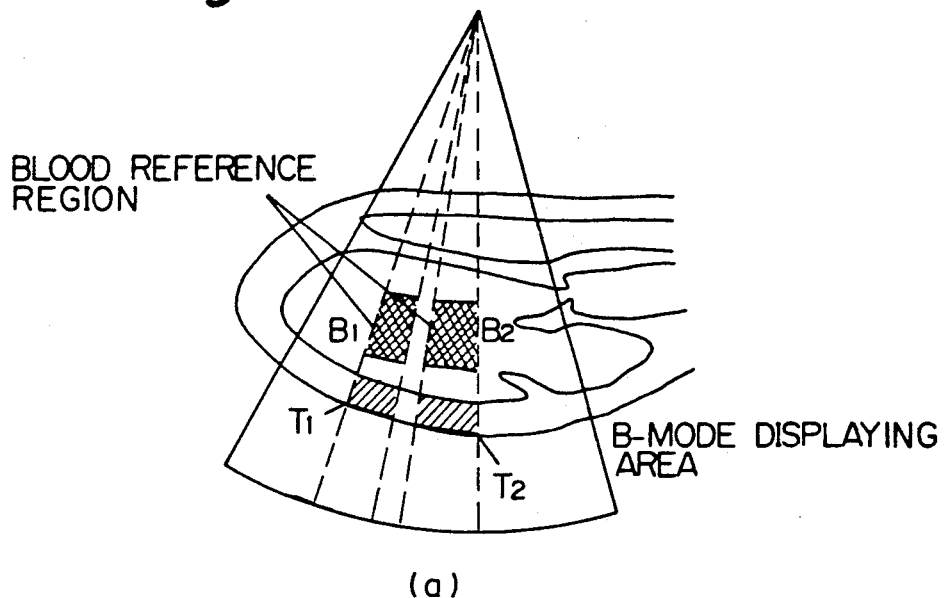

FIG. 14A indicates calculation portions of scattering coefficients of tissues T1 and T2, and blood reference regions B1 and B2 by using a display area of a B-mode image.

Figure 14B:
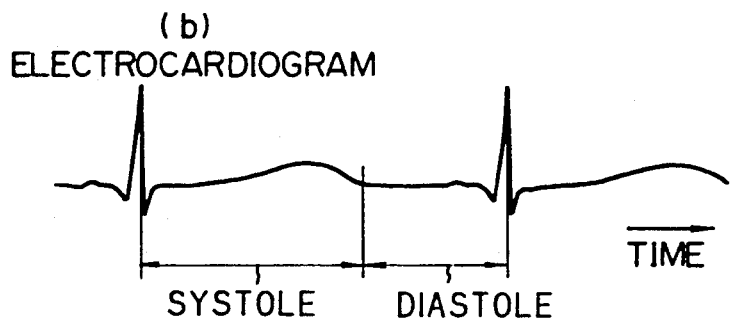

FIG. 14B indicates an electrocardiogram.

FIG. 14C indicates an example of displaying a changing state with time of the scattering coefficient n of the tissues T1 and T2.

FIG. 14D indicates an example of displaying a changing state with time of the scattering coefficient b of tissues T1 and T2.

FIG. 14E indicates a marker in a blood reference time phase.

FIG. 14F indicates an example of a color coded image of scattering coefficients on an M-mode image. Note, FIGS. 14A to 14F can be voluntarily indicated on the display unit in any combination.

FIGS. 15A to 15D are diagrams showing an example of displaying scattering coefficients.

FIG. 15A indicates scattering coefficients b and n, which are indicated by a color indication, on a B-mode image with a color flow image (CFI). Furthermore, an ROI for indicating a region of reference blood is also indicated. In this diagram, the color flow image and the scattering coefficients b and n are simultaneously indicated, but it can be constituted that the color flow image and the scattering coefficients b and n are separately indicated by different displays, or the scattering coefficients b and n only are indicated.

Figure 15B:
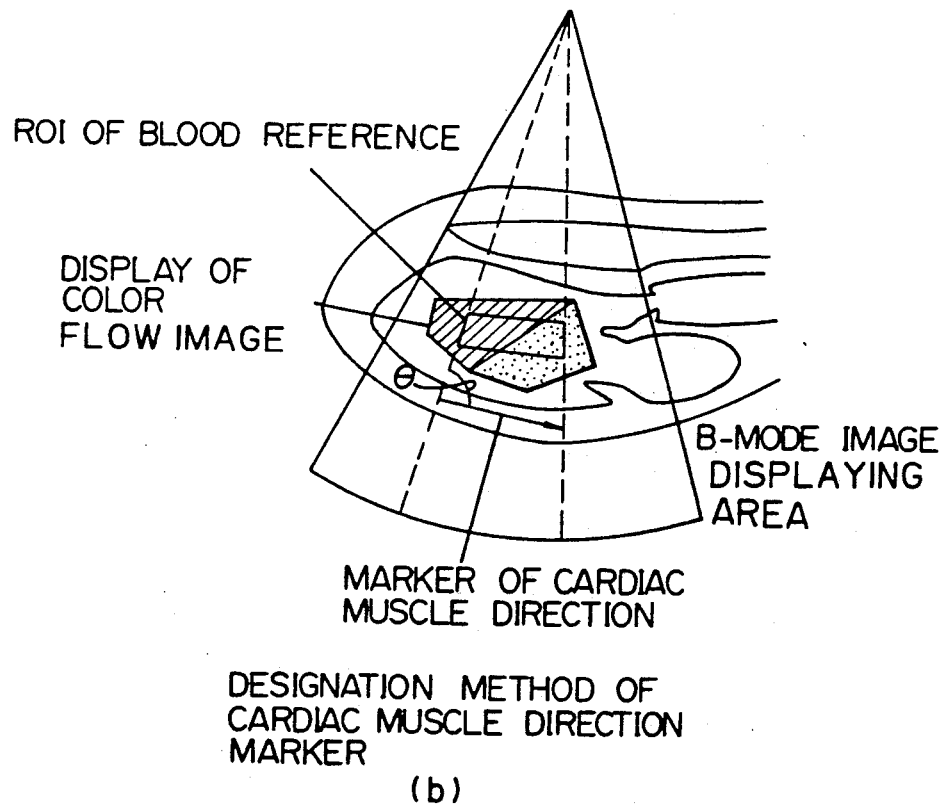
Figure 15C:
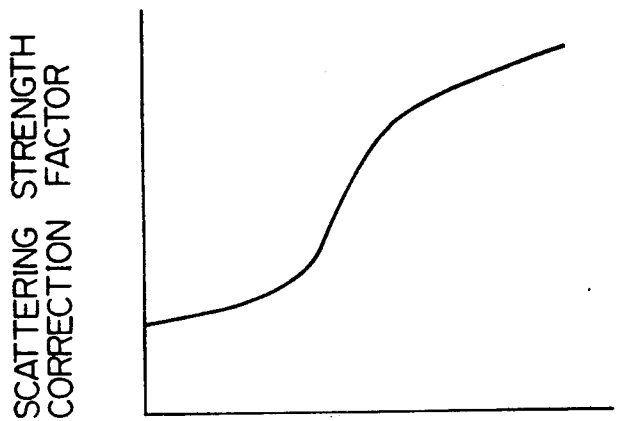

FIG. 15B indicates a marker which is externally established at the state of freezing of the B-mode image or the CFI to indicate a cardiac muscle direction. Note, it is well known that the scattering coefficients vary depending on an angle between a scanning direction and the musle. FIG. 15C indicates an example of the factor to correct the angle dependency.

Figure 15D:
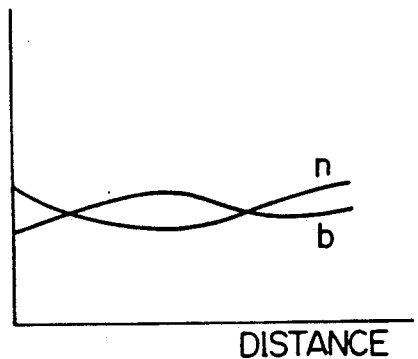

FIG. 15D indicates an explanatory example of one-dimensional profile of profiles scattering coefficients b and n of the tissues with reference to blood. Namely, the display unit 9 can display spatial scattering coefficients b and n of the tissues as a profile.

According to the second aspect of the present invention as in the above descriptions, blood scattering power spectrum at a portion of tissues of an object of measurement is estimated by using scattering power spectrum of blood which has a definite ultrasound scattering characteristic, the scattering power spectrum of the tissues of the object of measurement is normalized (divided) by the estimated scattering power spectrum, and scattering coefficients b and n are obtained and displayed, so that the scattering coefficients b and n of the tissues can be exactly estimated without being influenced by the attenuation. Furthermore, these estimated scattering coefficients b and n of the tissues are displayed on the display unit accompanied with a B-mode image, an electrocardiogram, and the like, so that diagnostic accuracy can be increased.

Many widely differing embodiments of the present invention may be constructed without departing from the spirit and scope of the present invention, and it should be understood that the present invention is not limited to the specific embodiments described in this specification, except as defined in the appended claims.

We claim:

1. Ultrasound diagnostic equipment for calculating and displaying an integrated backscatter of an organ comprising:
   means for receiving electrical signals representative of an ultrasound beam reflected from a tissue region and a blood region of an organ to a probe of an ultrasound diagnostic equipment;
   a tissue power means, connected to said receiving means to be supplied with received signals of said diagnostic equipment, for calculating tissue scattering power of tissues in said tissue region of an object of measure in said organ;
   a blood power means, connected to said receiving means to be supplied with said received signals, for calculating scattering power of blood in said blood region of said organ and estimating blood scattering power at the region of a portion of the tissues of said object of measurement by using said calculated scattering power of the blood;
   an integrated backscatter means, connected to said tissue power means and said blood power means, for normalizing said tissue scattering power by determining a quotient using said calculated tissue scattering power and said estimated blood scattering power, and for calculating an integrated backscatter by said normalized tissue scattering power; and
   a display means, connected to said integrated backscatter means, for displaying a representation of said calculated integrated backscatter.

2. Ultrasound diagnostic equipment as claimed in claim 1, wherein said tissue power means comprises:
   a power unit, supplied with said received signals, for calculating scattering power of the tissues in said organ; and
   a tissue spatial average unit, connected to said power unit, for deriving a spatial average of the scattering powers of the tissues in said organ obtained by each scanning line.

3. Ultrasound diagnostic equipment as claimed in claim 1, wherein said blood power means includes means for calculating an average of said blood scattering powers for each duration of blood flow speed exceeding threshold levels or for each duration of blood scattering power exceeding a threshold level, and estimating blood scattering power at said portion of the tissues of said object of measurement by using said calculated average scattering power of the blood.

4. Ultrasound diagnostic equipment as claimed in claim 1, wherein said blood power means comprises:
   a low pass filter having $f^{-n}$ characteristics wherein f is signal frequency and n is a scattering coefficient, supplied with said received signals;
   a doppler detector, connected to said low pass filter, for calculating a blood flow speed and a blood flow power;
   a duration unit, connected to said doppler detector, for detecting a duration of blood flow speed exceeding threshold levels and a duration of blood flow power exceeding a threshold level;
   a correction unit, connected to said doppler detector, for correcting a variable factor of the blood scattering power due to an individual difference of volume percentage of blood corpuscle in each human and for correcting for a variation of the scattering power of the blood against the blood flow speed;
   an external designation unit, for externally designating a duration where the blood scattering power is calculated;
   an average unit, connected to said duration unit, said correction unit and said external designation unit, for averaging the scattering powers of said blood in one of a duration detected by said duration unit and a duration designated by external designation unit;
   an interpolation unit, connected to said average unit, for interpolating each average scattering power of said blood by an m-th order interpolation;
   an attenuation correction unit, connected to said interpolation unit, for correcting blood power in accordance with a difference of attenuation from the position of said blood to the position of said tissues; and
   a blood spatial average unit, connected to said attenuation correction unit and said integrated backscatter means, for deriving a spatial average of the scattering powers of said blood obtained by each scanning line.

5. Ultrasound diagnostic equipment as claimed in claim 4, wherein said doppler detector includes a quadrature detector, an MTI-filter, a flow unit, and a doppler power unit.

6. Ultrasound diagnostic equipment as claimed in claim 1, wherein said integrated backscatter means comprises:
   an ROI-setting unit, supplied with said received signals, for designating one of an ROI and a marker, and for activating a function of moving the respective ROI or marker in accordance with a wall-movement;
   a normalizing unit, connectd to said tissue power means and said blood power means, for calculating an integrated backscatter; and
   an angle correction unit, connected to said calculated normalizing unit, for correcting said integrated backscatter according to an angle between a cardiac muscle direction and said ultrasound beam.

7. Ultrasound diagnostic equipment as claimed in claim 1, wherein said ultrasound diagnostic equipment further comprises an image means, supplied with said received signals, for generating selected images including a B-mode image, a color flow image and an M-mode image, so that said display means displays both said integrated backscatter of the tissues and each said selected image.

8. Ultrasound diagnostic equipment according to claim 1, wherein said display means includes means to display said integrated backscatter of the tissues as a time varying graph.

9. Ultrasound diagnostic equipment according to claim 1, wherein said display means includes means for displaying a representation of said integrated backscatter of the tissues accompanied with an electrocardiogram.

10. Ultrasound diagnostic equipment according to claim 1, wherein said display means includes means for selectively displaying a marker and a color at one of a duration of blood flow speed exceeding threshold levels and a duration of blood flow power exceeding threshold level.

11. Ultrasound diagnostic equipment according to claim 1, wherein said display means includes means for displaying a one dimensional integrated backscatter profile along a designated direction.

12. Ultrasound diagnostic equipment according to claim 1, wherein said ultrasound diagnostic equipment includes means for displaying information for diagnosing a myocardial infarction of a heart.

13. Ultrasound diagnostic equipment for calculating and displaying an integrated backscatter of an organ wherein said ultrasound diagnostic equipment comprises:
- a probe including means for radiating an ultrasound beam to an optional portion of an organ using electrical pulses and for receiving ultrasound waves scattered from said optional portion and converting the received ultrasound waves to received electrical signals;
- a transmitting circuit, for generating electrical pulses in accordance with a predetermined timing;
- a transmitting amplifier, connected between said probe and said transmitting circuit, for amplifying said electrical pulses and driving said probe;
- a receiving amplifier, connected to said probe, for amplifying electrical signals produced by ultrasound waves received by said probe;
- a tissue power unit, connected to said receiving amplifier, including means for calculating scattering power of a tissue region of an object of measurement in said organ;
- a blood power unit, connected to said receiving amplifier, including means for calculating scattering power of a blood region of the object of measurement in said organ, and for estimating blood scattering power at the tissue region by using said calculated scattering power of the blood;
- an integrated backscatter unit, connected to said tissue power unit and said blood power unit, including means for normalizing said tissue scattering power calculated by said tissue power unit by using said blood scattering power estimated by said blood power unit, and for calculating an integrated backscatter;
- an image unit, connected to said receiving amplifier, including means for generating selected images including a B-mode image, a color flow image and an M-mode image; and
- a display unit, connected to said integrated backscatter unit and said image unit, including means for displaying a representation of said integrated backscatter calculated by said integrated backscatter unit and any of said B-mode image, said color flow image and said M-mode image.

14. Ultrasound diagnostic equipment as claimed in claim 13, wherein said tissue power unit comprises:
- a power unit, supplied with said received signals, for calculating scattering power of said tissue region; and
- a tissue spatial average unit, connected to said power unit, for deriving a spatial average of the scattering powers of said tissue region obtained by each scanning line.

15. Ultrasound diagnostic equipment as claimed in claim 13, wherein blood power unit includes means for calculating an average of said blood scattering powers for each duration of blood flow speed exceeding threshold levels or for each duration of blood scattering power exceeding a threshold level, and estimating blood scattering power at the tissue region by using said calculated average scattering power of the blood.

16. Ultrasound diagnostic equipment as claimed in claim 13, wherein said blood power unit comprises:
- a low pass filter having $f^{-n}$ characteristics wherein f is signal frequency and n is a scattering coefficient, supplied with said received signals;
- a doppler detector, connected to said low pass filter, for calculating a blood flow speed and a blood flow power;
- a duration unit, connected to said doppler detector, for detecting a duration of blood flow speed exceeding threshold levels and a duration of blood flow power exceeding a threshold level;
- a correction unit, connected to said doppler detector, for correcting a variable factor of the blood scattering power due to an individual difference of volume percentage of blood corpuscle in each human, and for correcting a variation of the scattering power of the blood region against the blood flow speed;
- an external designation unit, for externally designating a duration where the blood scattering power is calculated;
- an average unit, connected to said duration unit, said correction unit and said external designation unit, for averaging the scattering powers of said blood region in one of a duration detected by said duration unit and a duration designated by said external designation unit;
- an interpolation unit, connected to said average unit, for interpolating each average scattering power of said blood region by an m-th order interpolation;
- an attenuation correction unit, connected to said interpolation unit, for correcting blood power in accordance with a different of attenuation from said blood region to said tissue region; and
- a blood spatial average unit, connected to said attenuation correction unit and said integrated backscatter unit, for deriving a spatial average of the scattering powers of said blood region obtained by each scanning line.

17. Ultrasound diagnostic equipment as claimed in claim 16, wherein said doppler detector includes a quadrature detector, an MTI-filter, a flow unit, and a doppler power unit.

18. Ultrasound diagnostic equipment as claimed in claim 13, wherein said integrated backscatter unit comprises:
- an ROI-setting unit, supplied with said received signals, for designating one of an ROI and a marker, and for activating a function of moving the respective ROI or marker in accordance with a wall-movement;
- a normalizing unit, connected to said tissue power unit and said blood power unit, for calculating an integrated backscatter; and
- an angle correction unit, connected to said normalizing unit, for correcting said integrated backscatter according to an angle between a cardiac muscle direction and said ultrasound beam.

19. Ultrasound diagnostic equipment according to claim 13, wherein said display unit includes means to display said integrated backscatter of the tissue region as a time varying graph.

20. Ultrasound diagnostic equipment according to claim 13, wherein said display unit includes means for displaying said integrated backscatter of the tissues accompanied with an electrocardiogram.

21. Ultrasound diagnostic equipment according to claim 13, wherein said display unit includes means for selectively displaying a marker and a color at a duration of blood flow speed exceeding threshold levels or a duration of blood flow power exceeding a threshold level.

22. Ultrasound diagnostic equipment according to claim 13, wherein said display unit includes means for displaying a one-dimentional integrated backscatter profiled along a designated direction.

23. Ultrasound diagnostic equipment according to claim 13, wherein said ultrasound diagnostic equipment includes means for displaying information for diagnosing a myocardial infarction of a heart.

24. Ultrasound diagnostic equipment for calculating and displaying scattering coefficients of backscatter of an organ comprising:
 means for receiving electrical signals representative of an ultrasound beam reflected from a tissue region and a blood region of an organ to a probe of an ultrasound diagnostic equipment;
 a tissue power spectrum means, connected to said receiving means to be supplied with said received signals, for calculating scattering power spectrum of tissues in said tissue region, of an object of measurement said organ;
 a blood power spectrum means, connected to said receiving means to be supplied with said received signals, for calculating scattering power spectrum of blood in said blood region of said organ and estimating blood power spectrum at the region of a portion of the tissues of said object of measurement by using said calculated scattering power spectrum of the blood;
 a scattering coefficient means, connected to said tissue power spectrum means, connected to said tissue power spectrum means and said blood power spectrum means for normalizing said tissue scattering power spectrum by determining a quotient using said calculated scattering power spectrum of tissues and said estimated blood scattering power spectrum, and for calculating scattering coefficients b and n of the tissues of the object of measurement in said organ by using said normalized tissue scattering power spectrum wherein, when said normalized tissue scattering spectrum is plotted on a graph with the ordinate representing scattering power in dB and the abscissa representing a logarithm of scattering power frequency, the point where the plot crosses the ordinate at zero frequency represents scattering coefficient b and the slope of the normalized spectrum plot line represents scattering coefficient n; and
 a display means, connected to said scattering coefficient means, for displaying said scattering coefficient b and n.

25. Ultrasound diagnostic equipment as claimed in claim 24, wherein said tissue power spectrum means comprises:
 a power spectrum unit, supplied with said received signals, for calculating scattering power spectrum of the tissue in said organ; and
 a tissue spatial average unit, connected to said power spectrum unit, for deriving a spatial average of the scattering power spectra of the tissues in said organ obtained by each scanning line.

26. Ultrasound diagnostic equipment as claimed in claim 24, wherein said blood power spectrum means includes means for calculating an average of said blood scattering power spectra for each duration of blood flow speed exceeding threshold levels and for each duration of blood scattering power exceeding a threshold level, and for estimating blood scattering power spectrum at the portion of the tissues of said object of measurement by using said calculated average scattering power spectrum of the blood.

27. Ultrasound diagnostic equipment as claimed in claim 24, wherein said blood power spectrum means comprises:
 a low pass filter having $f^{-n}$ characteristics wherein f is a signal frequency and n is a scattering coefficient, supplied with said received signals;
 a doppler detector, connected to said low pass filter, for calculating a blood flow speed, a blood flow power and scattering power spectrum of the blood;
 a duration unit, connected to said doppler detector, for detecting a duration of blood flow speed exceeding threshold levels and a duration of blood flow power exceeding a threshold level;
 a correction unit, connected to said doppler detector, for correcting a variable factor of the blood scattering power spectrum due to an individual different of volume percentage of blood corpuscle in each human, and for correcting the scattering power spectrum of the blood against the blood flow speed;
 an external designation unit, for externally designating a duration where the scattering power spectrum of the blood is calculated;
 an average unit, connected to said duration unit, said correction unit and said external designation unit, for averaging the scattering power spectra of said blood in one of a duration detected by said duration unit and a duration designated by said external designation unit;
 an interpolation unit, connected to said average unit, for interpolating frequency components of each average scattering power spectrum of blood by an m-th order interpolation;
 an attenuation correction unit, connected to said interpolation unit, for correcting blood power spectrum in accordance with a difference of attenuation characteristics from the position of said blood to the position of said tissues; and
 a blood spatial average unit, connected to said attenuation correction unit and said scattering coefficient means, for deriving a spatial average of the scattering power spectra of said blood obtained by each scanning line.

28. Ultrasound diagnostic equipment as claimed in claim 27, wherein said doppler detector includes a quadrature detector, an MTI-filter, a flow unit, and a doppler power spectrum unit.

29. Ultrasound diagnostic equipment as claimed in claim 28, wherein said MTI-filter is applied to a series of data obtained by repeatedly transmitting ultrasound pulses in the same direction, and said equipment includes means for carrying out a complex Fourier translation for data series of output from said MTI-filter for each transmitting, and said blood power spectrum is calculated by using results of said complex Fourier transformation.

30. Ultrasound diagnostic equipment as claimed in claim 24, including means for modifying each frequency component of said blood power spectrum and said tissue power spectrum so that the number of samples on the frequency axis become the same for each power spectrum.

31. Ultrasound diagnostic equipment as claimed in claim 24, wherein said scattering coefficient means comprises:
    an ROI-setting unit, supplied with said received signals, including means for designating one of an ROI and a marker, and for activating a function of moving the respective ROI or marker in accordance with a wall-movement;
    a normalizing unit, connected to said tissue power spectrum means and said blood power spectrum means, including means for calculating scattering coefficients b and n; and
    an angle correction unit, connected to said normalizing unit, including means for correcting said scattering coefficients b and n according to an angle between a cardiac muscle direction and said ultrasound beam.

32. Ultrasound diagnostic equipment as claimed in claim 24, wherein said ultrasound diagnostic equipment further comprises an image means, supplied with said received signals, for generating selected images including a B-mode image, a color flow image and and M-mode image, so that said display means displays both said scattering coefficients b and n of the tissue and each said selected.

33. Ultrasound diagnostic equipment as claimed in claim 24, wherein said scattering coefficient means includes means for plotting an oblique line with a linear approximation by applying a method of least squares to the normalized tissue scattering power spectrum.

34. Ultrasound diagnostic equipment according to claim 24, wherein said display means includes means for displaying said scattering coefficients b and n of the tissues as a time varying graph.

35. Ultrasound diagnostic equipment according to claim 24, wherein said display means includes means for displaying said scattering coefficient b and n of the tissues accompanied with an electrocardiogram.

36. Ultrasound diagnostic equipment according to claim 24, wherein said display means includes means for displaying one of a marker, a color at a duration of blood flow speed exceeding threshold levels and a duration of blood flow power exceeding a threshold level.

37. Ultrasound diagnostic equipment according to claim 24, wherein said display means includes means for displaying a one-dimentional scattering coefficients b and n profile along a designated direction.

38. Ultrasound diagnostic equipment according to claim 24, wherein said ultrasound diagnostic equipment includes means for displaying information for diagnosing a myocardial infraction of a heart.

39. Ultrasound diagnostic equipment for calculating and displaying scattering coefficients of an organ from received signals comprising:
    a probe including means for radiating an ultrasound beam to an optional portion of an organ using electrical pulses and receiving ultrasound waves scattered from said organ optional portion and converting the received ultrasound waves to received electrical signals;
    a transmitting circuit, for generating electrical pulses in accordance with a predetermined timing;
    a transmitting amplifier, connected between said probe and said transmitting circuit, for amplifying said electrical pulses and driving said probe;
    a receiving amplifier, connected to said probe, for amplifying electrical signals produced by ultrasonic waves received by said probe;
    a tissue power spectrum unit, connected to said receiving amplifier, including means for calculating scattering power spectrum of a tissue region of an object of measurement in said organ.
    a blood power spectrum unit, connected to said receiving amplifier, including means for calculating scattering power spectrum of a blood region of the object of measurement in said organ, an for estimating blood scattering power spectrum at a portion of the tissue region by using said calculated scattering power spectrum of the blood;
    a scattering coefficient unit, connected to said tissue power spectrum unit and said blood power spectrum unit, including means for normalizing said tissue power spectrum unit by using said blood scattering power spectrum estimated by said blood power spectrum unit, and for calculating scattering coefficients b and n, wherein said scattering coefficient n is determined by a slope of an oblique line of an orthographic plot of calculated tissue scattering power spectrum and said scattering coefficient b is determined by a crossing point of a Y-axis and said oblique line, where an X-axis represents a logarithm of scattering power frequency and said Y-axis represents a decibel expression of normalized scattering power;
    an image unit, connected to said receiving amplifier, including means for generating selected images including a B-mode image, a color flow image and an M-mode image; and
    a display unit, connected to said scattering coefficient unit and said image unit, including means for displaying said scattering coefficients b and n calculated by said scattering coefficient unit and any of said B-mode image, said color flow image and said M-mode image generated by said image unit.

40. Ultrasound diagnostic equipment as claimed in claim 39, wherein said tissue power spectrum unit comprises:
    a power spectrum unit, supplied with said received signals, for calculating scattering power spectrum of said tissue region; and
    a tissue spatial average unit, connected to said power spectrum unit, for deriving a spatial average of the scattering power spectra of said tissue region obtained by each scanning line.

41. Ultrasound diagnostic equipment as claimed in claim 39, wherein said blood power spectrum unit includes means for calculating an average of said blood scattering power spectra for each duration of blood flow speed exceeding threshold levels and for each duration of blood scattering power exceeding a threshold level, and for estimating blood scattering power spectrum at the tissue region by using said calculated average scattering power spectrum of the blood.

42. Ultrasound diagnostic equipment as claimed in claim 39 wherein said blood power spectrum unit comprises:
    a low pass filter having $f^{-n}$ characteristics wherein f is signal frequency and n is scattering coefficient, supplied with said received signals;

a doppler detector, connected to said low pass filter, for calculating a blood flow speed, a blood flow power and scattering power spectrum of said blood region;

a duration unit, connected to said doppler detector, for detecting a duration of blood flow speed exceeding threshold levels and a duration of blood flow power exceeding a threshold level;

a correction unit, connected to said doppler detector, for correcting a variable factor of the blood scattering power spectrum due to an individual difference of volume percentage of blood corpuscle in each human, and for correcting the scattering power spectrum of the blood region against the blood flow speed;

an external designation unit, for externally designating a duration where the scattering power spectrum of the blood is calculated;

an average unit, connected to said duration unit, said correction unit and said external designation unit, for averaging the scattering power spectra of said blood region in one of a duration detected by said duration unit and a duration designated by said external designation unit;

an interpolation unit, connected to said average unit, for interpolating optional frequency components of each average scattering power spectrum of said blood region by an m-th order interpolation;

an attenuation correction unit, connected to said interpolation unit, for correcting blood power spectrum in accordance with a difference of attenuation characteristics from said blood region to said tissue region; and a blood spatial average unit, connected to said attenuation correction unit and said scattering coefficient unit, for deriving a spatial average of the scattering power spectra of said blood region obtained by each scanning line.

43. Ultrasound diagnostic equipment as claimed in claim 42, wherein said doppler detector includes a quadrature detector, an MTI-filter, a flow unit, and a doppler power spectrum unit.

44. Ultrasound diagnostic equipment as claimed in claim 43, wherein said MTI-filter is applied to a series of data obtained by repeatedly transmitting ultrasound pulses in the same direction, and said equipment includes means for carrying out a complex Fourier transformation for data series of output from said MTI-filter for each transmitting, and said blood power spectrum is calculated by using results of said complex Fourier transformation.

45. Ultrasound diagnostic equipment as claimed in claim 39, including means for modifying each frequency component of said blood power spectrum and said tissue power spectrum so that the number of samples on the frequency axis become the same for each power spectrum.

46. Ultrasound diagnostic equipment as claimed in claim 39, wherein said scattering coefficient unit comprises:

an ROI-setting unit, supplied with said received signals, including means for designating one of the ROI and a marker, and for activating a function of moving the respective ROI or marker in accordance with a wall-movement;

a normalizing unit, connected to said tissue power spectrum unit and said blood power spectrum unit, including means for calculating scattering coefficients b and n; and an angle correction unit, connected to said normalizing unit, including means for correcting said scattering coefficients b and n according to an angle between a cardiac muscle direction and said ultrasound beam.

47. Ultrasound diagnostic equipment as claimed in claim 39, wherein said scattering coefficient means obtains an oblique line with a linear approximation by applying a method of least squares to the normalized tissue scattering power spectrum.

48. Ultrasound diagnostic equipment according to claim 39, wherein said display unit includes means for displaying said scattering coefficients b and n of the tissue region as a time varying graph.

49. Ultrasound diagnostic equipment according to claim 39, wherein said display unit includes means for displaying said scattering coefficients b and n of the tissue region accompanied with an electrocardiogram.

50. Ultrasound diagnostic equipment according to claim 39, wherein said display unit includes means for displaying one of a marker and a color at a duration of blood flow speed exceeding threshold levels and a duration of blood flow power exceeding a threshold level.

51. Ultrasound diagnostic equipment according to claim 39, wherein said display unit includes means for displaying one-dimentional scattering coefficients b and n profile along a designated direction.

52. Ultrasound diagnostic equipment according to claim 39, wherein said ultrasound diagnostic equipment includes means for displaying information for diagnosing a myocardial infarction of a heart.

* * * * *

UNITED STATES PATENT AND TRADEMARK OFFICE
CERTIFICATE OF CORRECTION

PATENT NO. : 5,097,836
DATED : March 24, 1992
INVENTOR(S) : Isamu YAMADA et al

It is certified that error appears in the above-identified patent and that said Letters Patent is hereby corrected as shown below:

On the cover page, in Item [54], delete "UNTRASOUND" and insert therefor -- ULTRASOUND --.

Signed and Sealed this

Sixth Day of July, 1993

Attest:

MICHAEL K. KIRK

Attesting Officer

Acting Commissioner of Patents and Trademarks